(12) United States Patent
Meijboom et al.

(10) Patent No.: US 10,508,200 B2
(45) Date of Patent: Dec. 17, 2019

(54) COMPOSITIONS COMPRISING TRIBLOCK COPOLYMERS

(71) Applicant: INGELL TECHNOLOGIES HOLDING B.V., Groningen (NL)

(72) Inventors: Ronald Meijboom, Groningen (NL); Paul Marcel Van Midwoud, Groningen (NL); Maarten Van Dijk, Groningen (NL); Theodorus Adrianus Cornelius Flipsen, Groningen (NL); Esther De Boef, Groningen (NL)

(73) Assignee: INGELL TECHNOLOGIES HOLDING B.V., Groningen (NL)

( * ) Notice: Subject to any disclaimer, the term of this patent is extended or adjusted under 35 U.S.C. 154(b) by 0 days.

(21) Appl. No.: 15/772,992

(22) PCT Filed: Nov. 4, 2016

(86) PCT No.: PCT/EP2016/076698
§ 371 (c)(1),
(2) Date: May 2, 2018

(87) PCT Pub. No.: WO2017/077054
PCT Pub. Date: May 11, 2017

(65) Prior Publication Data
US 2019/0211206 A1    Jul. 11, 2019

(30) Foreign Application Priority Data
Nov. 4, 2015    (EP) .................................... 15193024

(51) Int. Cl.
*C08L 71/02*    (2006.01)
*A61L 27/18*    (2006.01)
(Continued)

(52) U.S. Cl.
CPC ............ *C08L 71/02* (2013.01); *A61K 9/0024* (2013.01); *A61K 9/107* (2013.01); *A61K 47/10* (2013.01);
(Continued)

(58) Field of Classification Search
None
See application file for complete search history.

(56) References Cited

U.S. PATENT DOCUMENTS

2013/0017189 A1* 1/2013 Pierre .................. A61K 9/0024
424/130.1

FOREIGN PATENT DOCUMENTS

| WO | 0182970 A1 | 11/2001 |
| WO | 2012131106 A1 | 10/2012 |
| WO | 2015059358 A1 | 4/2015 |

OTHER PUBLICATIONS

Jo, S. et al., Reverse Thermal Gelation of Aliphatically Modified Biodegradable Triblock Copolymers, Macromol. Biosci, 2006, vol. 6, No. 11, XP-55004254A, pp. 923-928.
(Continued)

*Primary Examiner* — Rachel Kahn
(74) *Attorney, Agent, or Firm* — Hudak, Shunk & Farine Co. LPA

(57) ABSTRACT

A composition including a) 55-98.9 wt % of at least one type of triblock copolymer (A) of formula (1)

R—B-A-B—R    (1)

b) 0.1-15 wt % of at least one surfactant (B) and c) 1-30 wt % of water, wherein A is a hydrophilic block having a number average molecular weight (Mn) of 100-1,000 Da, B is a hydrophobic block made from monomers having at least a monomer B1 and a monomer B2, wherein B1 and B2 have the largest weight contents in the hydrophobic block and B1 has a lower molecular weight than B2, wherein R is an end
(Continued)

IVR of formulations with water and lidocaine-HCL or lysozyme group which is H or a C1-C30 organic moiety, wherein the composition is fluid in a temperature range of 0° C. to 37° C., wherein the weight % are relative to the sum of a), b) and c), and wherein the sum of components a), b) and c) is at least 80 wt % of the entire composition, preferably at least 90 wt %; to the use of the composition and to pharmaceutical compositions having said composition and an active pharmaceutical ingredient.

23 Claims, 10 Drawing Sheets

(51) Int. Cl.
    *A61L 27/54* (2006.01)
    *A61K 9/00* (2006.01)
    *A61K 47/10* (2017.01)
    *A61K 47/34* (2017.01)
    *A61K 9/107* (2006.01)
    *C08G 63/664* (2006.01)
    *A61L 27/58* (2006.01)

(52) U.S. Cl.
    CPC .............. *A61K 47/34* (2013.01); *A61L 27/18* (2013.01); *A61L 27/54* (2013.01); *A61L 27/58* (2013.01); *C08G 63/664* (2013.01); *A61L 2400/06* (2013.01); *C08L 2203/02* (2013.01)

(56) References Cited

OTHER PUBLICATIONS

Yu, L, et al., Mixing a Sol and a Precipitate of Block Copolymers with Different Block Ratios Leads to an Injectable Hydrogel, Biomacromolecules, 2009, vol. 10, No. 6, XP-002586070, pp. 1547-1553.

World Health Organization, International Statistical Classification of Diseases and Related Health Problems, 10th Revision, Version for 2007, processed 2006, copyright WHO/DIMDI 1994/2006, pp. 1-21.

Japanese Office Action/Translation dated Sep. 25, 2018.

\* cited by examiner

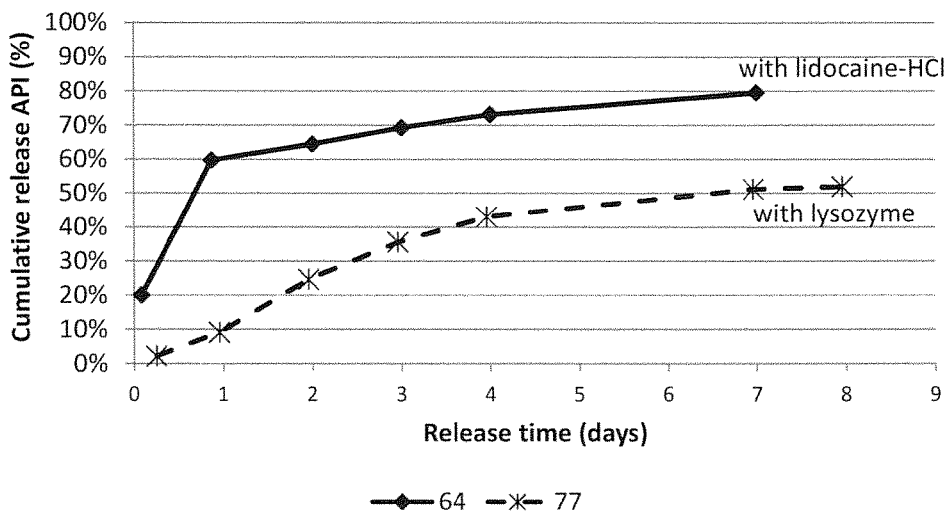
FIG. 1: IVR of formulations with water and lidocaine-HCL or lysozyme
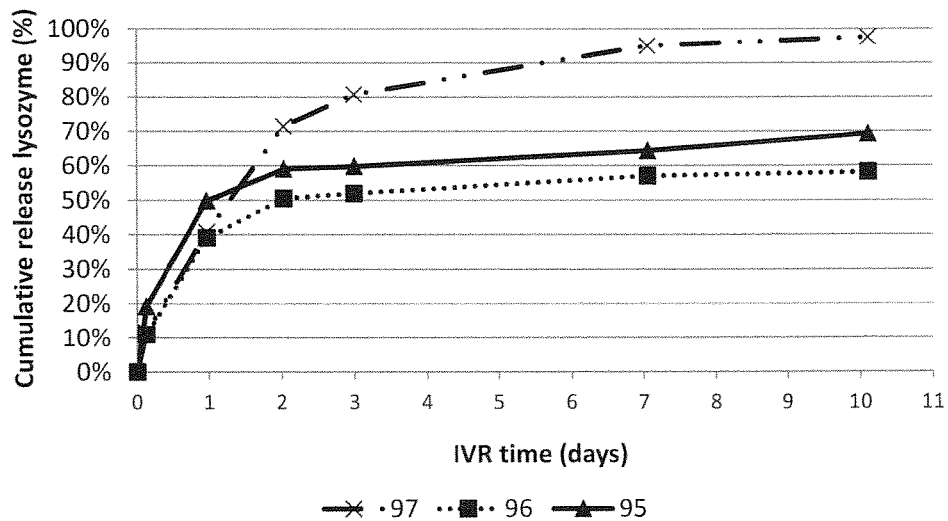
FIG. 2: IVR formulations with commercial surfactants

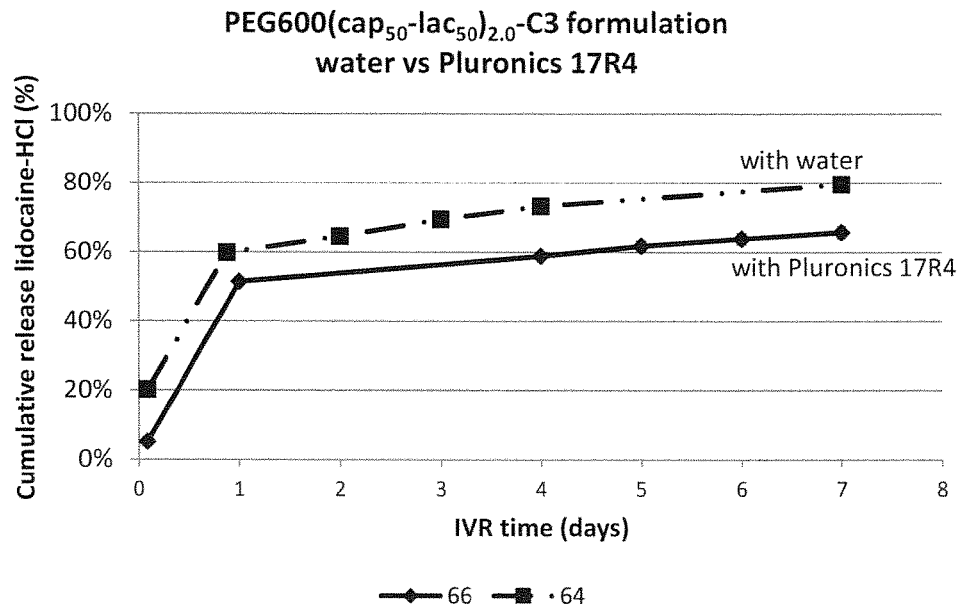
FIG. 3: IVR of formulation with Lidocaine-HCL
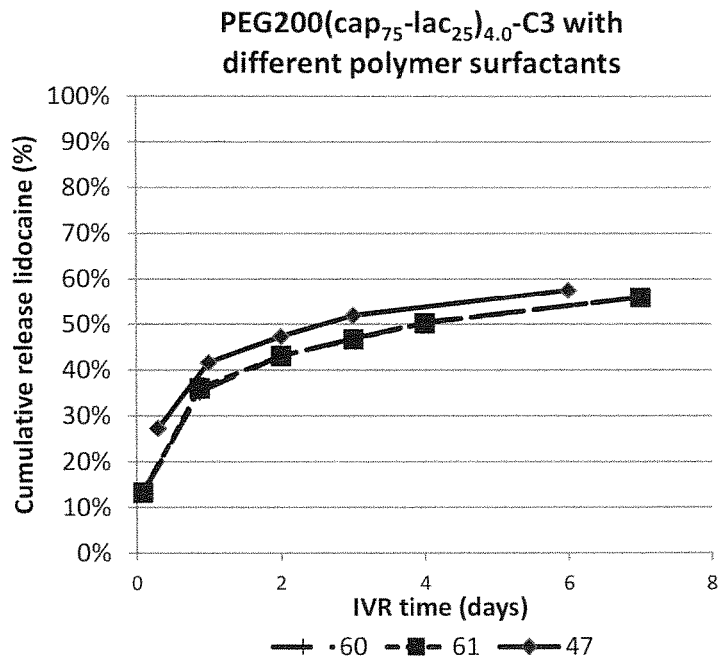
FIG. 4: PEG200(cap$_{75}$-lac$_{25}$)$_{4.0}$-C3 with different polymer surfactants

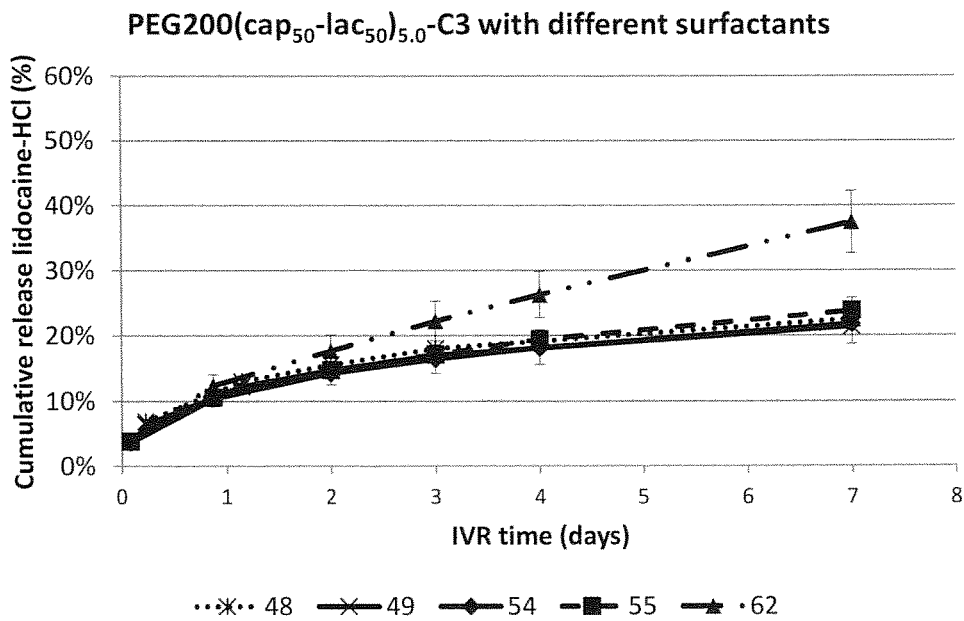
FIG. 5: PEG200(cap$_{50}$-lac$_{50}$)$_{5.0}$-C3 with different surfactants and without surfactant (loading 1% lidocaine-HCl)
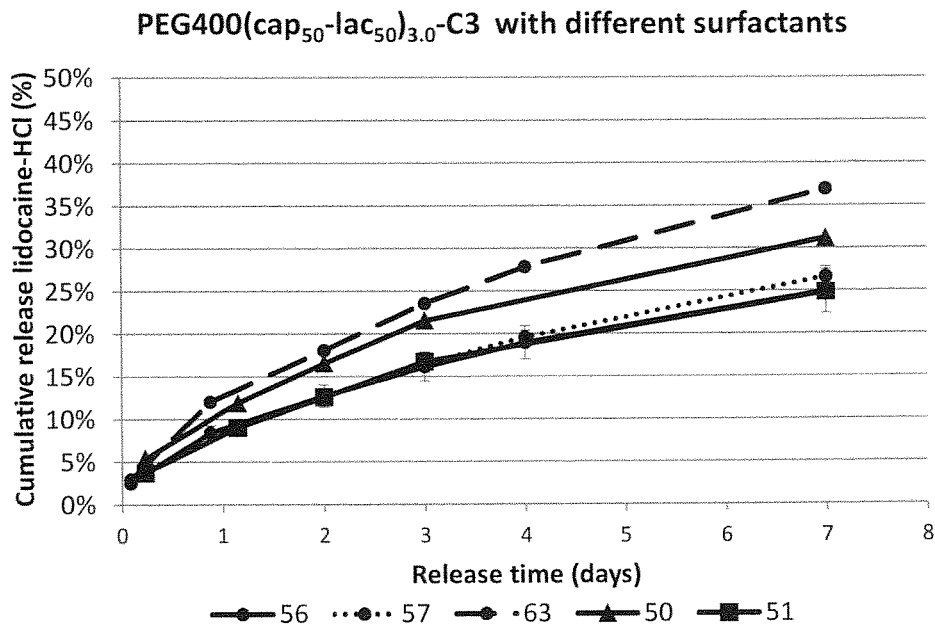
FIG. 6: PEG400(cap$_{50}$-lac$_{50}$)$_{3.0}$-C3 with different surfactants and without surfactant (loading 1% lidocaine-HCl)

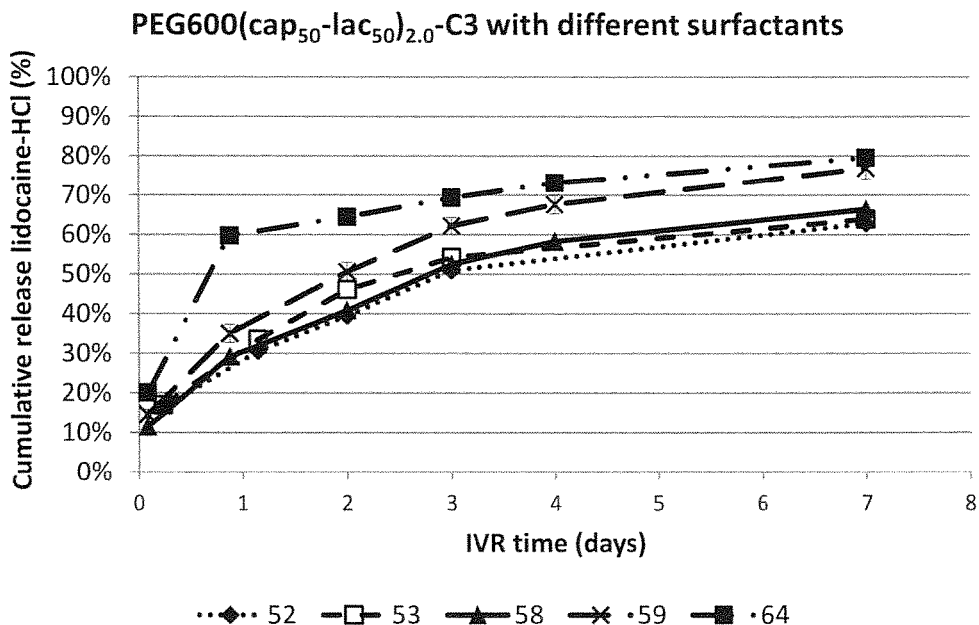
FIG. 7: PEG600(cap$_{50}$-lac$_{50}$)$_{2.0}$-C3 with different surfactants and without surfactant (loading 1% lidocaine-HCl)
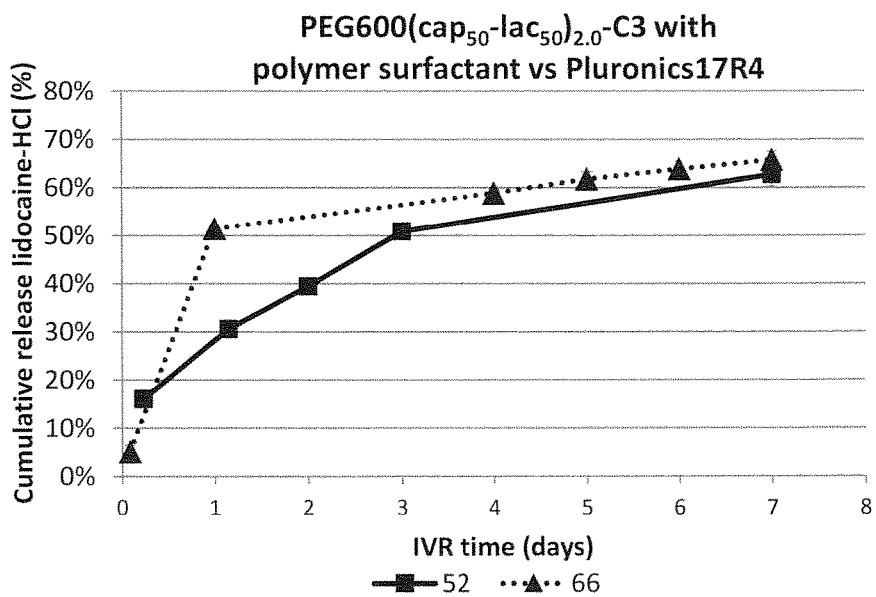
FIG. 8: Formulation with Pluronics17R4

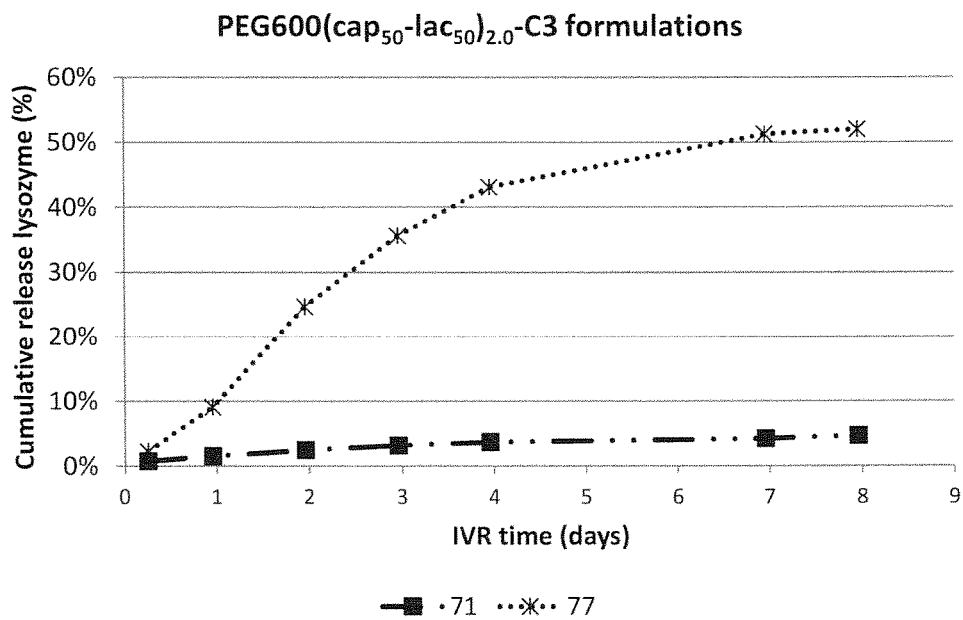
FIG. 9: PEG600(cap50-lac50)2.0-C3 formulations with and without surfactant, loaded with 1% lysozyme
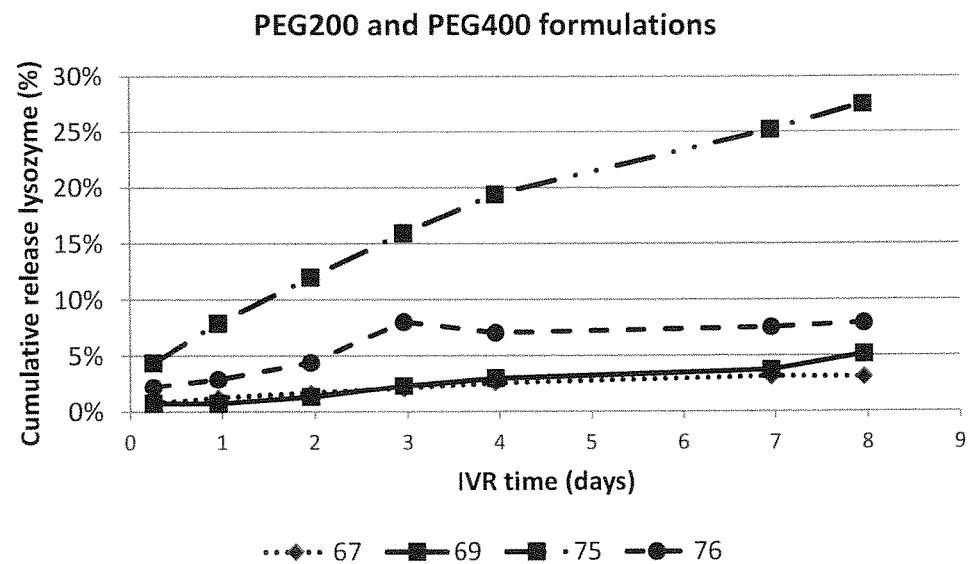
FIG. 10: PEG200 and PEG400 formulations with and without polymer surfactants, loaded with 1% lysozyme

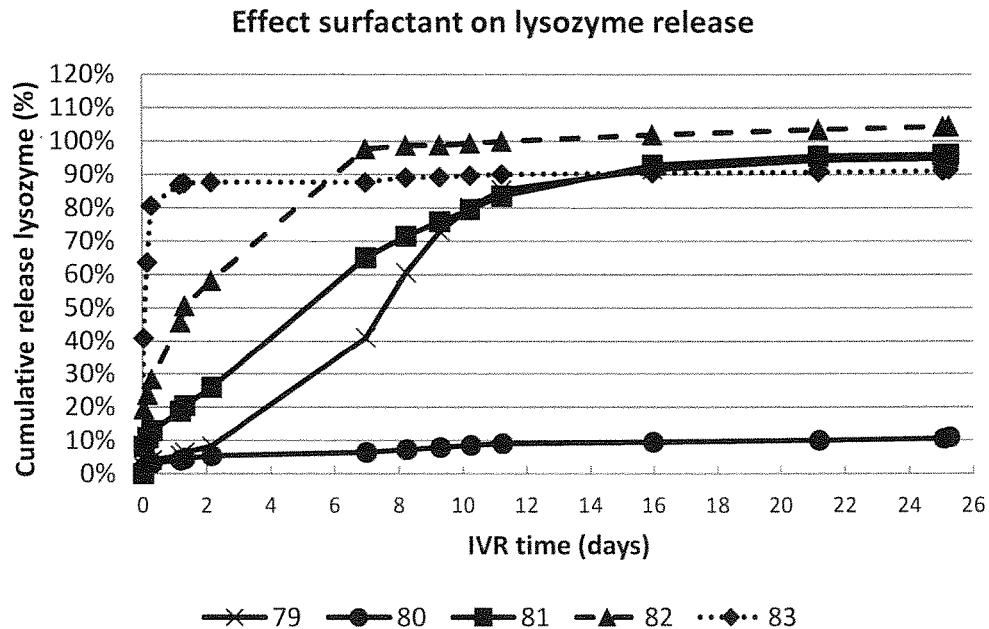
FIG. 11: Effect of a surfactant on lysozyme release (loading 1%)
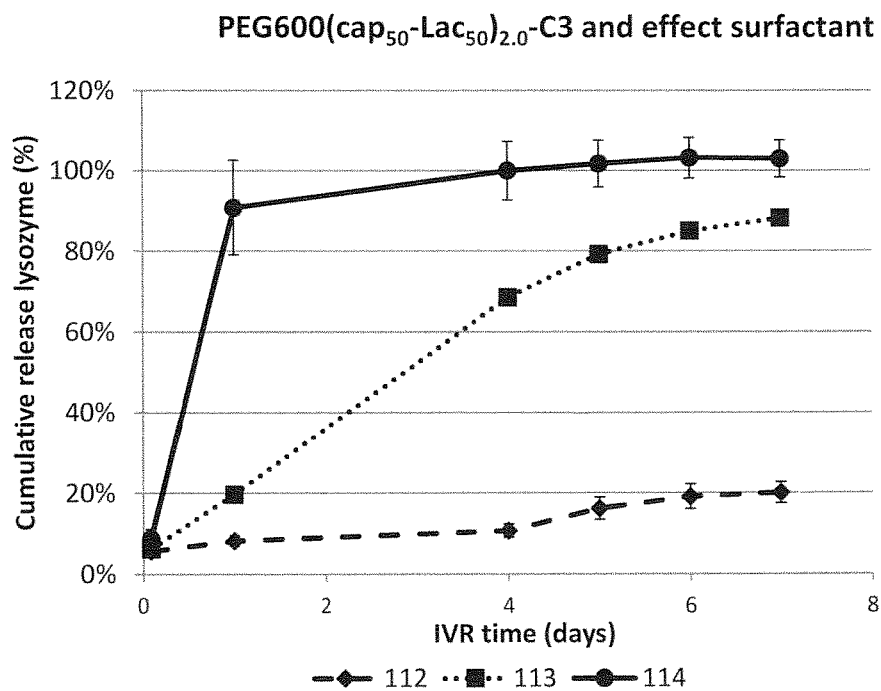
FIG. 12: Effect of surfactants on the IVR

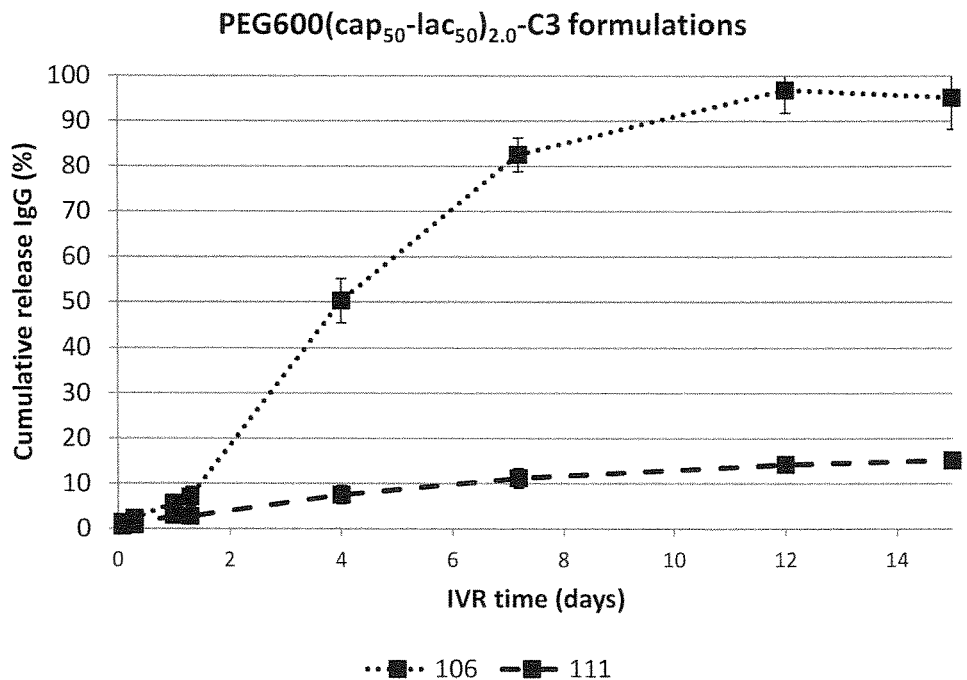
FIG. 13: PEG600(cap$_{50}$-lac$_{50}$)$_{2.0}$-C3 formulations loaded with 2.5 mg/ml IgG
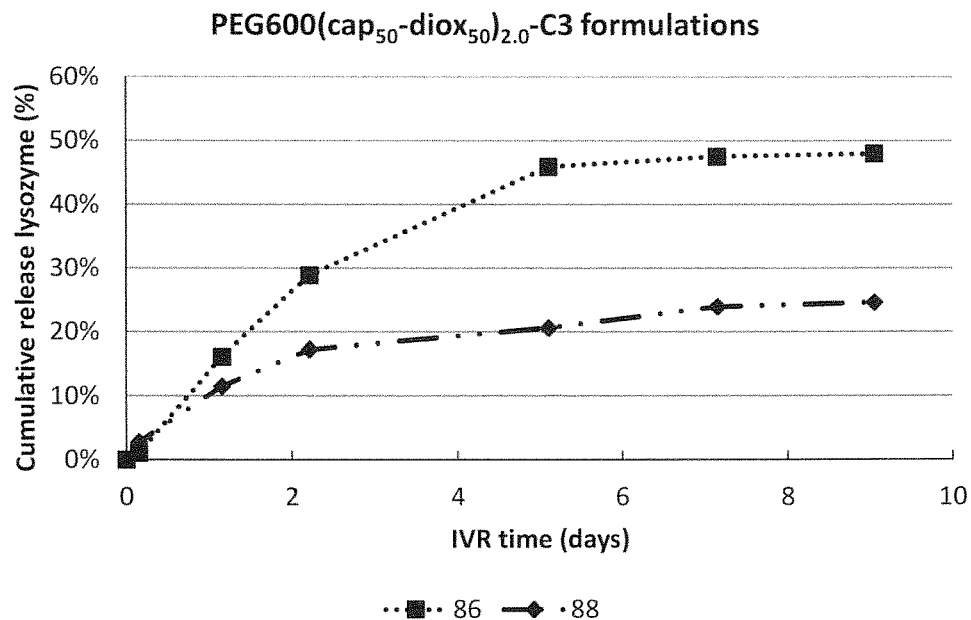
FIG. 14: PEG600(cap$_{50}$-diox$_{50}$)$_{2.0}$-C3 triblock copolymer with different surfactants, loading 1% lysozyme

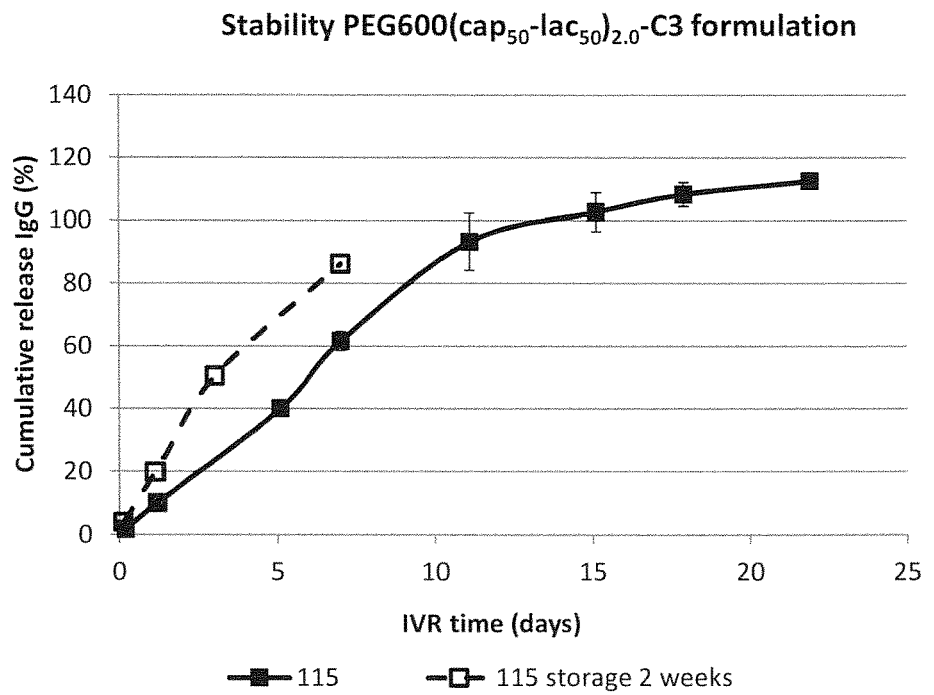
FIG. 15: IVR of formulation 115, directly after preparation and after 2 weeks storage.
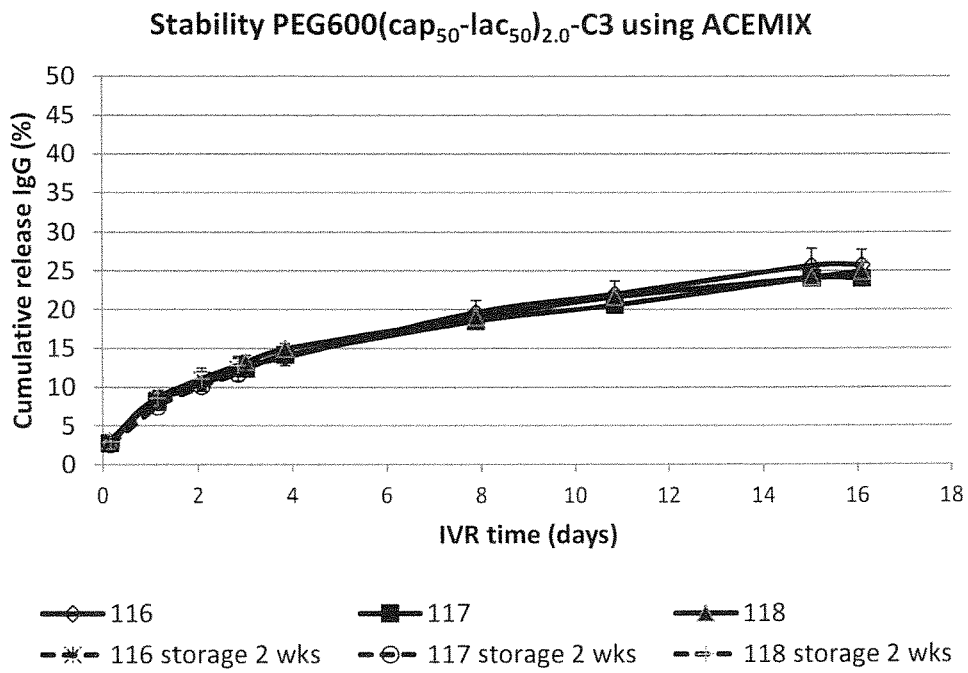
FIG. 16: IVR of IgG from PEG600(cap$_{50}$-lac$_{50}$)$_{2.0}$-C3 formulations with two surfactants

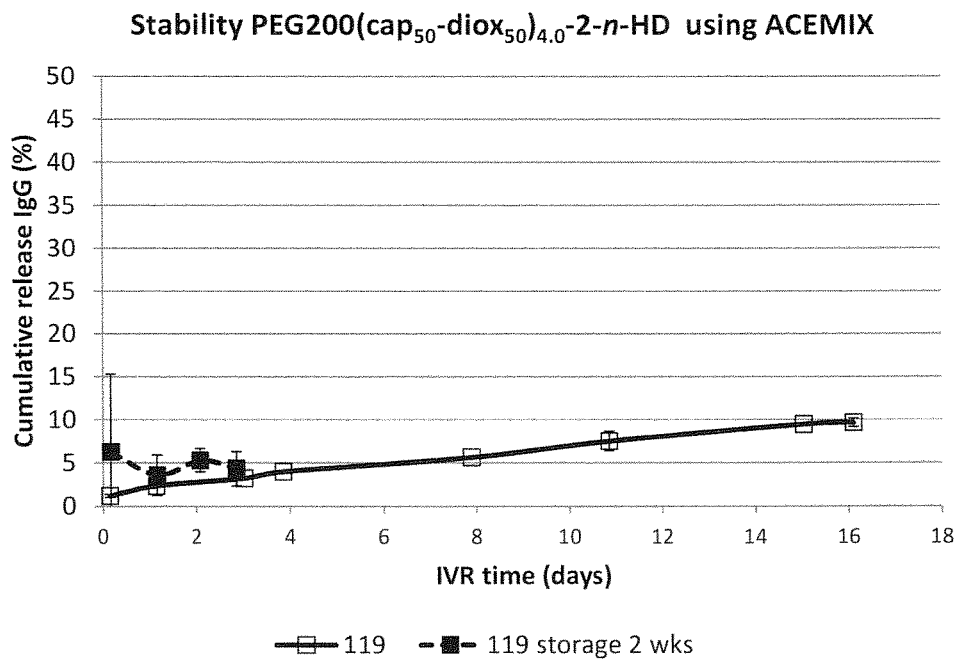
FIG. 17: IVR of lysozyme from PEG200(cap$_{50}$-diox$_{50}$)$_{4.0}$-2-*n*-HD formulation with two surfactants
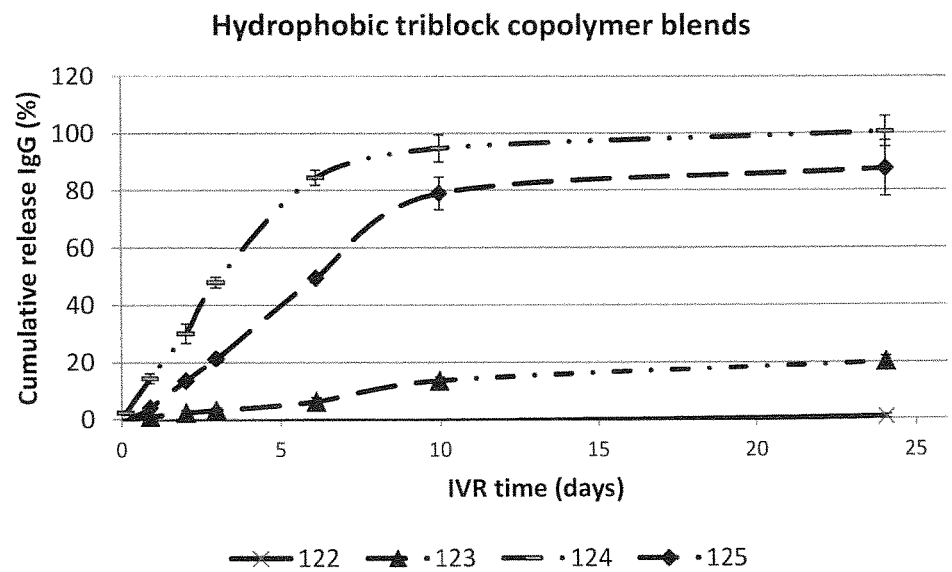
FIG. 18: IVR of hydrophobic triblock copolymer blends loaded with IgG

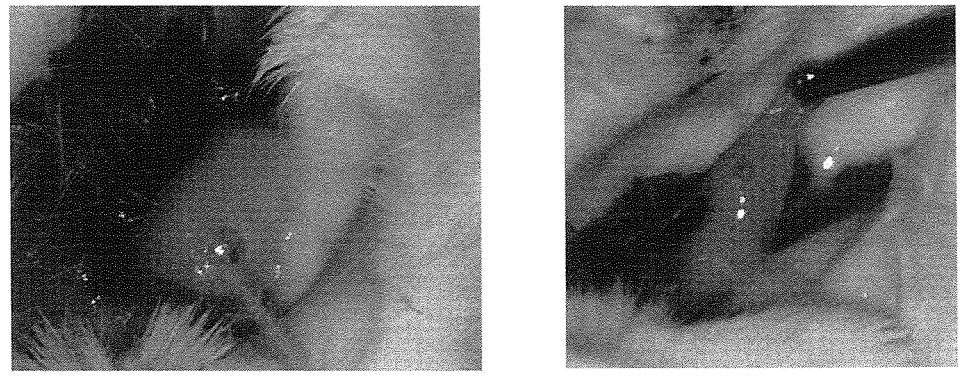
FIG. 19: Ex-vivo experiment

COMPOSITIONS COMPRISING TRIBLOCK COPOLYMERS

FIELD OF THE INVENTION

The invention relates to a composition that contains at least one bioresorbable triblock copolymer being liquid at ambient conditions, intimately blended with a bioresorbable surfactant and water, all together forming a stable water in oil (w/o) emulsion. The compositions can be suitable for injection into a human or animal body. After injection into said body the emulsions form a (semi-)solid cohesive mass. These liquid compositions allow encapsulation of a hydrophilic active pharmaceutical ingredient (API) and after injection into a body slowly release said active pharmaceutical ingredient. These compositions can also function as a medical device after injection into a body either or not in combination with biologically active agents.

BACKGROUND OF THE INVENTION

Controlled release of active pharmaceutical ingredients, also named biologically active agents or therapeutically active agents, has become essential in treatments of humans and animals. Especially of interest is controlled release of active pharmaceutical ingredients locally in a body, such as in tissues or organs for either direct on-site treatment or for systemic uptake.

In recent years, a number of bioresorbable polymers fabricated into product shapes as microspheres, strands, rods and the like have been developed for this reason. The active pharmaceutical ingredient is incorporated into the interior of the polymer product and is after administration to the human or animal body slowly released by different mechanisms. One of the downsides of these products is the laborious process of incorporating the active ingredient in their interior, which may involve either organic solvents or elevated temperatures. These processes can result in the inactivation of the active ingredient during the process.

Numerous examples of liquid BAB block copolymers can be found in literature. Disadvantages of the prior art block copolymers are, however, that they are used in combination with solvent or liquid polymer additives to make injectable pharmaceutical compositions. In some cases the BAB block copolymers have rather high molecular weights and low molecular weight polymers like for example polyethylene glycol are added to make the composition injectable. In other cases the liquid BAB block copolymer are used as plasticizers for higher molecular weight block copolymers to make an injectable composition and/or to dissolve an API in the liquid polymer. Addition of these low molecular weight polymers give rise to high burst releases, and an unwanted fast release of the low molecular weight polymer, which may give negative physiological side effects. The incorporation of hydrophilic API's in these systems is also troublesome. In some examples water is added and mixed through the liquid polymer, which however show burst release and relatively short release times of the hydrophilic API. In yet many other cases water is added to prepare thermoreversible gels, which however show burst release and relative short release times of the hydrophilic API.

SUMMARY OF THE INVENTION

The object of the present invention is to provide a formulation, which is a water in oil (w/o) emulsion of at least one bioresorbable triblock copolymer, a bioresorbable surfactant and water, which address one or more of the above and/or other disadvantages, and can be produced by ways of a robust and simple process.

The object is achieved by a composition comprising
a) 55-98.9 wt % of at least one type of triblock copolymer (A) of formula (1)

R—B-A-B—R     (1)

b) 0.1-15 wt % of at least one surfactant (B) and
c) 1-30 wt % of water,
wherein A is a hydrophilic block having a number average molecular weight (Mn) of 100-1,000 Da, B is a hydrophobic block made from monomers comprising at least a monomer B1 and a monomer B2, wherein B1 and B2 have the largest weight contents in the hydrophobic block and B1 has a lower molecular weight than B2, wherein R is an end group which is H or a C1-C30 organic moiety, wherein the composition is fluid in a temperature range of 0° C. to 37° C., wherein the weight % are relative to the sum of a), b) and c), and wherein the sum of components a), b) and c) is at least 80 wt % of the entire composition, preferably at least 90 wt %.

The relatively low Mn of the A block of the triblock copolymer (A) results in the copolymer (A) being relatively hydrophobic. With the help of the surfactant (B), an emulsion of droplets of an aqueous phase dispersed in a continuous phase of the copolymer (A) is formed.

An advantage of the composition according to the invention is that a stable emulsion is obtained containing a rather hydrophobic triblock copolymer (A) and a surfactant with water. Such emulsion can be used as a carrier for hydrophilic active pharmaceutical ingredients, such as small molecule drugs, peptides, proteins and genetic materials. In these cases a pharmaceutical composition can be obtained wherein the hydrophilic active pharmaceutical ingredient is completely dissolved in the aqueous phase of the emulsion.

An advantage of the composition according to the invention is that a formulation is obtained wherein the viscosity is much lower than the 'hydrophobic' triblock copolymer according to formula 1 per se, which may improve the injectability, significantly.

Another advantage is that the compositions of the present invention can be used to incorporate API's that are only available in an aqueous solution.

A further advantage of the compositions according to the invention is that the release of an active pharmaceutical ingredient is well-controlled and a burst release directly after administration is significantly less or almost absent compared to systems of the prior art.

Another advantage of the composition according to the invention is that the emulsions form a (semi-)solid, once injected into the body of a human or animal, that allows the use for tissue filling, tissue separation or other medical purposes. Such use could well be without any active pharmaceutical ingredient, but if the therapy requires such, could be a combination with therapeutically or biologically active agents.

a) RBABR Hydrophobic Triblock Copolymer (A)

A bioresorbable polymer is herewith defined as a polymer that can be metabolized by and/or secreted from the body.

The hydrophobic triblock copolymer (A) according to the invention is preferably fluid at the entire temperature range between 0° C. and 37° C.

Notwithstanding the foregoing, the copolymer may also show fluid behaviour outside this temperature range. The term fluid may also be replaced by liquid, but for the invention both refer to a polymer that is in a fluid state without the help of any solvent or plasticizer.

The fluid behaviour of the hydrophobic triblock copolymers, according to the invention, is measured by its dynamic viscosity under shear. The dynamic viscosity was measured using a TA Instruments AR2000Ex rheometer with a plate-cone setup, type 40 mm cone, angle 1:00:00 deg:min:sec. During the viscosity measurement, the temperature was kept constant at either 20° C. or 37° C., with a shear rate of 5 $s^{-1}$ during 300 s. Average viscosity values were calculated using software (Trios software, TA Instruments). In this way the average dynamic (shear) viscosity of the polymer is determined. The viscosity determined at 37° C. preferably has a value below 30 Pa·s, more preferably below 20 Pa·s or below 10 Pa·s, below 5 Pa·s, below 3 Pa·s, below 2 Pa·s, or most preferably below 1 Pa·s. Typically the viscosity at 37° C. is above 0.1 Pa·s.

The viscosity determined at 20° C. typically has a value above 0.1 Pa·s. The viscosity determined at 20° C. preferably has a value below 30 Pa·s, more preferably below 20 Pa·s or below 10 Pa·s, most preferably below 5 Pa·s.

The viscosity of the hydrophobic triblock copolymers (A) according to the invention ranges between 0.1 and 30 Pa·s at a temperature of 20° C., preferably between 0.2 and 20 Pa·s, most preferably between 0.3 and 10 Pa·s.

The hydrophobic triblock copolymers (A) used in the present invention have preferably low to very low glass transition temperatures. The glass transition temperature ($T_g$) is determined by differential scanning calorimetry (DSC, second heating curve with heating of 2 celc/min)) and defined as the midpoint of the thermal transition. The copolymer preferably has a $T_g$ (midpoint) below −20° C., more preferably below −30° C. and most preferably below −40° C.

The triblock copolymers of the invention are preferably fully amorphous or at least have preferably very low melt temperatures. The melt temperature ($T_m$) is determined by differential scanning calorimetry (DSC, second heating curve with heating of 2 celc/min)) and defined as the midpoint of the thermal transition. The copolymer preferably has no detectable melt peak or a $T_m$ (midpoint) below 20° C., more preferably below 10° C. and most preferably below 0° C.

The number average molecular weight (Mn) of the triblock copolymer (A) preferably is between 500-5,000 Da, more preferably within the range of 600-3,000 Da and most preferably within the range of 700-2,500 Da. The number average molecular weight (Mn) used herein can be determined with size exclusion chromatography as defined in the experimental section.

The block ratio, in the context of the invention, is the ratio between the sum of the number average molecular weights (Mn) of both hydrophobic blocks without counting the end-group modification (the sum of the two B blocks) and the hydrophilic A-block. The required block ratio depends on the composition of the hydrophilic A-block, the hydrophobic block composition (i.e. B-blocks), the degree of modification and the nature of the organic end-group.

In an embodiment of the invention the block ratio, defined as the ratio between the sum of the number average molecular weight of the B-blocks and the number average molecular weight of the A-block, ranges between 0.3 and 20, preferably between 0.5 and 10.

In the present invention, the organic end-groups reduce the viscosity of the triblock copolymers and with that improve their injectability. The organic end-group also has a remarkable effect on controlling the release kinetics of a loaded active pharmaceutical ingredient. More in particular, the organic end-group slows down the release of a loaded active pharmaceutical ingredient.

The amount of the RBABR block copolymer (A) ranges between 55-98.9 wt % relative to the total of the composition. Typically it may be at least 60 wt %, 70 wt %, 80 wt %, 90 wt % of the composition. It may be less than 98 wt %, 95 wt % or 92 wt %.

A Moiety

The A block in the hydrophobic triblock copolymer (A) is a hydrophilic polymer block. Preferably, the A block is chosen from the group consisting of polyethylene glycol (PEG), polypropylene oxide (PPO), polytetramethylene oxide (PTMO), copolymers of PEG and PPO, polyvinylpyrrolidone (PVP), poly [N-(2-hydroxyethyl)-L-glutamine] (PHEG) or a poly(2-oxazoline). Polyethylene glycol is a diol also known as poly(ethylene oxide) (PEO) and both names can be used interchangeably for the purpose of this invention.

More preferably, the A block is PEG, most preferably the A block is a linear PEG.

The A block has a number average molecular weight (Mn) of at least 100 Da, preferably at least 120 Da and most preferably at least 150 Da. The number average molecular weight of the A block preferably is at most 1,000 Da. For example the number average molecular weight of the A block is between 180-700 Da. The molecular weight of the A block such as PEG is chosen such that is does not crystallize or only slowly once being part of the hydrophobic triblock copolymers of the current invention. An important aspect is the result the particular A block, such as PEG, has on the viscosity of the hydrophobic triblock copolymer obtained with it.

B Moiety

The hydrophobic triblock copolymer (A) comprises two B blocks flanking the A block. The B blocks are hydrophobic. B is a hydrophobic block made from monomers comprising at least a monomer B1 and a monomer B2. This means that B may be made from two monomers or made from three or more monomers.

B1 and B2 have the largest weight contents in the hydrophobic block, i.e. the monomers present in the hydrophobic block in the largest amounts are referred as B1 and B2. Of the monomers having the largest weight contents in the hydrophobic block, the one with a lower molecular weight is referred as B1 and the monomer with a higher molecular weight is referred as B2.

Accordingly, when B is made from two monomers, these two monomers are referred as B1 and B2. For example, when B is made from caprolactone (M=114) and lactide (M=144), B1 is caprolactone and B2 is lactide.

When B is made from three or more monomers, the monomers which are present in the largest amounts are referred as B1 and B2. For example, when B is made from 50 wt % of caprolactone (M=114), 30 wt % of lactide (M=144) and 20 wt % of glycolide (M=116), B1 is caprolactone and B2 is lactide; when B is made from 20 wt % of caprolactone, 50 wt % of lactide and 30 wt % of glycolide, B1 is glycolide and B2 is lactide.

The monomers B1 and B2 may be cyclic monomers and each of the B blocks may have a number average molecular weight range between 200-1,500 Da. Preferably, the number average molecular weight of each B block ranges between 225-1,250 Da, more preferably between 250-1,000 Da, or between 300-800 Da.

Both B blocks can have the same or a different composition; preferably both B blocks have the same composition.

The monomers B1 and B2 may be cyclic monomers and may be selected from the group consisting of glycolide, lactide, ε-caprolactone, p-dioxanone (1,4-dioxan-2-one), trimethylene carbonate (1,3-dioxan-2-one), 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, chi.-diethylpropiolactone, ethylene carbonate, ethylene oxalate, 3-methyl-1,4-dioxane-2,5-dione, 3,3-diethyl-1,4-dioxan-2, 5-dione, 6,8-dioxabicycloctane-7-one, β-propiolactone, γ-butyrolactone, δ-valerolactone, ε-decalactone, 3-methyl-1,4-dioxane-2,5-dione, 1,4-dioxane-2,5-dione, 2,5-diketomorpholine, α,α-diethylpropiolactone, γ-butyrolactone, 1,4-dioxepan-2-one, 1,5-dioxepan-2-one, 6,6-dimethyl-dioxepan-2-one, 6,8-dioxabicycloctane-7-one, 5,5-dimethyl-1,3-dioxan-2-one, or preferably of the group consisting of glycolide, lactide, ε-caprolactone, δ-valerolactone, 1,3-dioxan-2-one (also known as trimethylene carbonate), 5,5-dimethyl-1,3-dioxan-2-one, 1,4-dioxan-2-one, 1,4-dioxepan-2-one and 1,5-dioxepan-2-one.

The monomers B1 and B2 are most preferably selected from the group consisting of glycolide, lactide, ε-caprolactone, δ-valerolactone, 1,3-dioxan-2-one (also known as trimethylene carbonate) and 1,4-dioxan-2-one (also known as p-dioxanone).

Hydrophobic blocks, containing the monomeric units described above, mainly contain ester and/or carbonate bonds, making them hydrolysable. They can be prepared in a range of well-defined molecular weights.

The choice of monomers B1 and B2 is based on how they affect the viscosity of the hydrophobic triblock copolymers obtained with them. Another important aspect is the effect they have on the rate and profile of bioresorption that one wants to achieve with the hydrophobic triblock copolymer in vivo. Polyesters made by combining aforementioned monomers have been studied for a while and some of the combinations are well-known.

In most cases, the combinations involve only 2 monomers B1 and B2, although examples with 3 different monomers in a B block are possible and can be beneficial.

In a preferred embodiment each B block (i.e. monomers B1 and B2) is a combination of ε-caprolactone with anyone of lactide, glycolide, δ-valerolactone, p-dioxanone or trimethylene carbonate; or a combination of δ-valerolactone with anyone of lactide, glycolide, p-dioxanone or trimethylene carbonate; or a combination of p-dioxanone with lactide, glycolide or trimethylene carbonate; or a combination of trimethylenecarbonate with lactide or glycolide; or a combination of lactide with anyone of δ-valerolactone, p-dioxanone.

The amount of the monomer B1 with respect to the total weight of the monomer B1 and the monomer B2, which is herein sometimes indicated by "X", may e.g. be 10-90 wt %, typically 20-80 wt %, 30-70 wt %, 40-60 wt % or 45-55 wt %.

R End-Groups

The hydrophobic triblock copolymer (A) used in the composition according to the invention comprises two R end-groups. B-A-B triblocks are modified by using the terminal hydroxyl group of the B blocks. Preferably, R is independently H or a C1-C30 organic moiety, more preferably R is a C1-C30 organic moiety. The organic moiety can be linear, cyclic or branched. The organic moiety may contain heteroatoms, like for example O, N and I. Examples of an organic moiety are fatty acid residues, ether residues or urethane residues. The fatty acid residue is obtained by the reaction of a fatty acid or activated fatty acid with the hydroxyl group of the end of a B-block. Fatty acids include a selection of saturated or unsaturated fatty acids of 1 to 30 carbon atoms, preferably 2 to 20 carbon atoms. The fatty acids groups can contain heteroatoms, like for example iodine. The presence of iodine can assist in visualizing the depot during and after injection into an animal or human body.

The C1-C30 fatty acid can be selected from the group consisting of formic acid, acetic acid, propionic acid, butyric acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, caproic acid, caprylic acid, capric acid, lauric acid, myristic acid, myristoleic acid, palmitic acid, palmitoleic acid, stearic acid, oleic acid, linoleic acid, alpha-linoleic acid, gamma-linoleic acid, stearidonic acid, rumenic acid, beta-calendic acid, eleostearic acid, puninic acid, parinaric acid, pinolenic acid, arachidic acid, eicosenoic acid, eicosadienoic acid, eicosatrienoic acid, dihomo-gamma-linolenic acid, mead acid, eicosatetraenoic acid, arachidonic acid, or eicosapentaenoic acid.

Preferably, R is chosen from an acetyl group, a propionyl group, a butyryl group, a pentanoyl group, a hexanoyl group, a nonanoyl group, a dodecanoyl group, a pentadecanoyl group, a 2-n-hexyldecanoyl group, a stearoyl group or a benzoyl group, wherein each R can be optionally substituted with heteroatoms like for example iodine. R can be linear, branched or cyclic and saturated or unsaturated.

Naturally occurring fatty acids are easily degradable through the acetyl-coenzyme A cycle. Furthermore these acids have less risk of exhibiting toxicity in vivo in quantities used in the scope of the present invention. Some of them could have beneficial or detrimental biological activities though. A person skilled in the art would have to take the choice of fatty acid into account in view of the application and the location in the body. Modification with longer fatty acid derivatives will generally increase the resorption time of the polymer.

Coupling fatty acids to the B-A-B triblock copolymers may involve the use of coupling agents like, but not limited to, isocyanates or the derivatisation of either the fatty acids or the polymer end-groups. Functional groups of the fatty acids or polymers can be activated to promote coupling by using activating agents like, but not limited to, carbonyl diimidazole, N-hydroxysuccinimide, para-nitrophenyl chloroformate, succinic anhydride. Direct derivatives of fatty acids like, but not limited to, acid chlorides, anhydrides, isocyanates can also be used, especially since some of them are readily commercially available.

These coupling methods are well-known to the one skilled in the art.

For some applications special moieties may have to be introduced into the fatty acid derivatives used for end group modification. For example, the use of an unsaturated fatty acid may allow chemical reactions to occur between the unsaturated fatty acid chains to achieve polymer crosslinking. Crosslinking is usually carried out in order to modify the mechanical properties and degradation profile of polymers. The activation and intermolecular reaction between those crosslinkable moieties is usually caused by a radiation source, an external chemical reaction or stimulus, or a combination thereof. Radiation examples include, but are not limited to, heat, infrared sources, ultra-violet sources, electron-beam sources, micro-waves sources, x-ray sources, visible light sources [monochromatic or not] and gamma-rays. External reaction, or stimulus include, but are not limited, to pH, oxidation/reduction reactions, reactions with a chemical agent present in vivo (gas, protein, enzymes, antibody etc.), reaction with a chemical added to the composition upon introduction into the body, known as dual systems, for example a molecule containing two or more reactive groups.

End-groups may also be chosen from the group of heteroatom alkyls, containing for instance oxygen, nitrogen or iodine atoms.

The choice of the end-group is based on the effect they have on the viscosity of the hydrophobic triblock copolymers obtained with them. Another important aspect is the effect they have on the formation of a (semi-) solid in vivo and on the softness thereof. Another important aspect is the effect they have on the release kinetics of a therapeutically active agent, if such an agent is incorporated in the (semi-) solid formed.

Preferred Block Copolymers

In one embodiment the hydrophobic triblock copolymer (A) according to formula 1 is a copolymer wherein A is a linear polyethylene glycol moiety having a number average molecular weight (Mn) between 150-1,000 Da, and wherein B stands for a polyester moiety comprising at least two types of monomers B1 and B2 chosen from the group consisting of ε-caprolactone, ε-valerolactone, glycolide, lactide, 1,4-dioxan-2-one (also known as p-dioxanone) and 1,3-dioxan-2-one (also known as trimethylene carbonate), more preferably form the group ε-caprolactone, δ-valerolactone, glycolide, lactide, wherein R is independently H or a C1-C30 fatty acid residue optionally containing heteroatoms and wherein the number average molecular weight (Mn) of the triblock copolymer is between 500-5,000 Da, preferably 600-3,000 Da, more preferably within the range of 700-2,500 Da; and wherein the shear viscosity determined at 20° C. has a value below 30 Pa·s, more preferably below 20 Pa·s or below 10 Pa·s, most preferably below 5 Pa·s; and wherein the copolymer has a $T_g$ (midpoint) below −20° C., more preferably below −30° C. and most preferably below −40° C.

In another embodiment the hydrophobic triblock copolymer (A) according to formula 1 is a triblock copolymer wherein the block ratio, which is defined as the ratio between the sum of the number average molecular weight of the B-blocks and the number average molecular weight of the A-block, ranges from 0.5 to 10, wherein the A-block is a linear polyethylene glycol block and wherein R is chosen from an acetyl group, a propionyl group, a hexanoyl group, a nonanoyl group, a dodecanoyl group, pentadecanoyl group, a stearoyl group or a benzoyl group and wherein each R can be optionally substituted.

In a further embodiment the hydrophobic triblock copolymer (A) according to formula 1 is a copolymer wherein A is a polyethylene glycol having a number average molecular weight (Mn) between 150-700 Da, wherein each B block is a combination of ε-caprolactone with anyone of lactide, glycolide, δ-valerolactone, p-dioxanone or trimethylene carbonate; or a combination of δ-valerolactone with anyone of lactide, glycolide, p-dioxanone or trimethylene carbonate; or a combination of p-dioxanone with lactide, glycolide or trimethylene carbonate; or a combination of trimethylene carbonate with lactide or glycolide; wherein the R is chosen from an acetyl group, a propionyl group, a hexanoyl group, a nonanoyl group, a dodecanoyl group, pentadecanoyl group, a stearoyl group or a benzoyl group and wherein each R can be optionally substituted, and wherein the number average molecular weight (Mn) of the entire block copolymer is between 750-3,000 Da, more preferably within the range of 1,000-2,500 Da; and wherein the shear viscosity determined at 20° C. has a value below 30 Pa·s, preferably below 20 Pa·s, more preferably below 10 Pa·s, most preferably below 5 Pa·s; and wherein the copolymer has a $T_g$ (midpoint) below −20° C., more preferably below −30° C. and most preferably below −40° C.

Surfactant (B)

The surfactant (B) applied in the present invention is preferably a bioresorbable surfactant. Surfactants can be divided in several classes, such as non-ionic, anionic and cationic surfactants. Examples of non-ionic surfactants are poloxamers (also known by the trade names Synperonics, Pluronics and Kolliphor) and polysorbates (like Tween-20 and Tween-80). Other non-ionic surfactants are polyvinylpyrrolidone (PVP) and polyvinylalcohol (PVA). Examples of anionic surfactants are ammonium lauryl sulfate, sodium lauryl sulfate, sodium lauryl ether sulfate (SLES), and sodium myreth sulfate. Examples of cationic surfactants are cetylpyridinium chloride, benzalkonium chloride and dimethyldioctadecylammonium chloride.

The present invention discloses bioresorbable non-ionic surfactants that are made up of amphiphilic linear, branched, grafted, comb-like or star-shaped block copolymers (diblock-, triblock or multi-block copolymers), hereafter also named 'polymer surfactants (B)'.

The amount of surfactant present in the composition is at least 0.1 wt %, 0.2 wt % or 0.3 wt %. Usually the amount of surfactant is less than 15 wt %, 10 wt % or 5 wt %, all relative to the sum of a), b and c). Preferably the amount of surfactant ranges between 0.2-15 wt %, 0.3-10 wt % or 0.3-5 wt %.

Preferred bioresorbable surfactants (B) are amphiphilic branched or linear copolymers (diblock-, triblock-, multi-block, graft and/or star-shaped copolymers). The preferred surfactants are molecules according to the formula 2 (polymer surfactant (B):

Rs-Bs-As-Bs-Rs            Formula 2 wherein As is a hydrophilic block having an number average molecular weight (Mn) of at least 1,000 Da, Bs is a hydrophobic block made from monomers comprising at least a monomer Bs1 and a monomer Bs2 wherein Bs1 and Bs2 have the largest weight contents in the hydrophobic block and Bs1 has a lower molecular weight than Bs2 and Rs is an end-group which is H or a C1-C30 organic moiety.

The polymer surfactant (B) (formula 2) may consist of the same types of blocks as the hydrophobic triblock copolymer (A) (formula 1), except that the molecular weight of the block As of the polymer surfactant (B) is higher than the molecular weight of the block A of the hydrophobic triblock copolymer (A).

The polymer surfactant (B) has a hydrophilic block As, which has a relatively high molecular weight, which results in the triblock copolymer (B) having a relatively hydrophilic character. It was surprisingly found that the addition of the polymer surfactant (B) to a composition comprising the hydrophobic triblock copolymer (A) and water results in an emulsion of water droplets, the aqueous phase, dispersed in a continuous phase of the hydrophobic triblock copolymer (A). Hence, although not wishing to be bound by any theory, it is thought that the hydrophilic triblock copolymer (B) acts as a surfactant.

Rs is preferably chosen from the group consisting of H, acetyl group, propionyl group, butyryl group, pentanoyl group, hexanoyl group, nonanoyl group, dodecanoyl group, pentadecanoyl group, 2-n-hexyldecanoyl group, stearoyl group or benzoyl group Preferably, the polymer surfactant (B) is an amphiphilic triblock copolymer (B), wherein As is a linear polyethylene glycol block, having a number average molecular weight (Mn) of between 1,000-3,000 Da, determined with size exclusion chromatography; wherein Bs are hydrophobic blocks comprising at least two cyclic monomers selected from the group consisting of lactide, ε-caprolactone, glycolide, p-dioxanone, trimethylene carbonate, ε-valerolactone, each Bs-block having a number average molecular weight (Mn) of between 400-3,000 Da, determined with size exclusion chromatography; and wherein Rs is an end-group of a H or a C1-C20 fatty acid residue.

Another preferred embodiment of the polymer surfactant (B) is a linear amphiphilic triblock copolymer (B) which has the property that at room temperature it is water-soluble and at an elevated temperature of 30° C. or higher it forms a bioresorbable hydrogel.

Preferably As is a PEG moiety. Preferably the number average molecular weight of the As moiety ranges between 1,000-3,000 Da, determined with size exclusion chromatography, preferably at least 1,250 Da, more preferably at least 1,500 Da.

In a preferred embodiment, the polymer blocks B and Bs comprise the same types of monomers, i.e. the monomer B1 and the monomer Bs1 are the same and the monomer B2 and the monomer Bs2 are the same.

The amount of the monomer B1 with respect to the total weight of the monomer B1 and the monomer B2, which is herein indicated by "X", may e.g. be 10-90 wt %, typically 20-80 wt %, 30-70 wt %, 40-60 wt % or 45-55 wt %.

The amount of the monomer Bs1 with respect to the total weight of the monomer Bs1 and the monomer Bs2, which is herein indicated by "Xs", may e.g. be 10-90 wt %, typically 20-80 wt %, 30-70 wt %, 40-60 wt % or 45-55 wt %.

Preferably, the difference between X and Xs is at most 40 wt %, more preferably at most 20 wt %, more preferably at most 10 wt %, more preferably at most 5 wt % and most preferably X is the same as Xs.

The advantage of having the same monomers in the B and Bs blocks (i.e. B1=Bs1 and B2=Bs2) is that the release rate of hydrophilic active pharmaceutical ingredients (API) from the composition surprisingly is decreased to a large extent. Very long release times can be reported, with a low or even very low burst release of said API's. Especially the presence of the same monomers in each B and Bs block in substantially the same ratio, gives a further increased release time of the API. In other words, if the polymer surfactant is in its chemical composition tailor-made to the hydrophobic triblock copolymer, forming the continuous phase of the emulsion, the release of said API's can be controlled surprisingly well.

One preferred embodiment of the polymer surfactant (B) is a linear amphiphilic triblock copolymer (B) wherein As is a linear polyethylene glycol block, having a number average molecular weight (Mn) of 1,250-1,750 Da, determined with size exclusion chromatography; wherein Bs are hydrophobic blocks comprising at least two cyclic monomers selected from the group consisting of lactide, ε-caprolactone and glycolide, each Bs-block having a number average molecular weight (Mn) of between 1,100-1,800 Da, determined with size exclusion chromatography; and wherein Rs is an end-group of a H or an acetyl, propionyl, hexanoyl or a dodecanoyl group.

Another preferred embodiment of the polymer surfactant (B) is a linear amphiphilic triblock copolymer (B) wherein As is a linear polyethylene glycol block, having a number average molecular weight (Mn) of 1,450-1,550 Da, determined with size exclusion chromatography; wherein Bs are hydrophobic blocks comprising at least two cyclic monomers selected from the group consisting of lactide, ε-caprolactone and each Bs-block having a number average molecular weight (Mn) of between 1,500-1,750 Da, determined with size exclusion chromatography; and wherein Rs is an end-group of an acetyl or propionyl group.

Another preferred embodiment of the polymer surfactant (B) is a linear amphiphilic triblock copolymer (B) wherein As is a linear polyethylene glycol block, having a number average molecular weight (Mn) of 1,450-1,550 Da, determined with size exclusion chromatography; wherein Bs are hydrophobic blocks comprising at least two cyclic monomers selected from the group consisting of lactide, ε-caprolactone and each Bs-block having a number average molecular weight (Mn) of between 1,300-1,400 Da, determined with size exclusion chromatography; and wherein Rs is an end-group of a H or an acetyl or propionyl group.

Another preferred embodiment of the polymer surfactant (B) is a linear amphiphilic diblock copolymer (B) wherein As is a linear methoxy polyethylene glycol block, having a number average molecular weight (Mn) of 1,000-3,000 Da, determined with size exclusion chromatography; wherein Bs is a hydrophobic block comprising at least two cyclic monomers selected from the group consisting of lactide, ε-caprolactone and the Bs-block has a number average molecular weight (Mn) of between 1,000-2,000 Da, determined with size exclusion chromatography; and wherein Rs is an end-group of a H or an acetyl or propionyl group.

In one embodiment, at least two polymer surfactants (B) are present in the composition. The addition of a second polymer surfactant (B) may further improve the long term stability of a composition, especially at lower temperatures between 1 and 8 Celcius.

Water Content

The composition according to the invention comprises water. The amount of water is preferably at least 1 wt %, 2 wt % or 4 wt %. Generally the amount of water is lower than 30 wt %, 20 wt % or 10 wt %, relative to the sum of components a), b) and c). The amount of water preferably ranges between 1-30 wt %, 2-20 wt % or 4-10 wt %.

Viscosity of the Composition

The composition according to the invention is fluid at the entire temperature range between 0° C. and 37° C.

Notwithstanding the foregoing, the composition may also show fluid behaviour outside this temperature range. The term fluid may also be replaced by liquid, but for the invention both refer to a composition that is in a fluid state without the help of any solvent or plasticizer.

The fluid behaviour of the composition, according to the invention, is measured by its dynamic viscosity under shear. The dynamic viscosity was measured using a TA Instruments AR2000Ex rheometer with a plate-cone setup, type 40 mm cone, angle 1:00:00 deg:min:sec. During the viscosity measurement, the temperature was kept constant at either 20° C. or 37° C., with a shear rate of 5 s$^{-1}$ during 300 s. Average viscosity values were calculated using software (Trios software, TA Instruments). In this way the average dynamic (shear) viscosity of the composition is determined. The viscosity determined at 37° C. preferably has a value below 30 Pa·s, more preferably below 20 Pa·s or below 10 Pa·s, below 5 Pa·s, below 3 Pa·s, below 2 Pa·s, or most preferably below 1 Pa·s. Typically the viscosity at 37° C. is above 0.1 Pa·s.

The viscosity determined at 20° C. typically has a value above 0.1 Pa·s. The viscosity determined at 20° C. preferably has a value below 30 Pa·s, more preferably below 20 Pa·s or below 10 Pa·s, most preferably below 5 Pa·s.

The viscosity of the composition according to the invention ranges between 0.1 and 30 Pa·s at a temperature of 20° C., preferably between 0.2 and 20 Pa·s, most preferably between 0.3 and 10 Pa·s.

Preferred Compositions of the Invention

In an embodiment the invention relates to a composition comprising:

a) 70-97.8 wt % of at least one type of hydrophobic triblock copolymer (A) of formula (1)

R—B-A-B—R     (1)

b) 0.2-10 wt % of at least one type of polymer surfactant (B) according to formula (2)

Rs-Bs-As-Bs-Rs     (2), and c) 2-20 wt % of water, wherein A is a hydrophilic block having an average molecular weight (Mn) of 100-1,000 Da, B is a hydrophobic block made from monomers comprising at least a monomer B1 and a monomer B2, wherein B1 and B2 have the largest weight contents in the hydrophobic block and B1 has a lower molecular weight than B2, wherein R is an end group which is H or a C1-C30 organic moiety;

wherein As is a hydrophilic block having an number average molecular weight (Mn) of at least 1,000 Da, Bs is a hydrophobic block made from monomers comprising at least a monomer Bs1 and a monomer Bs2 wherein Bs1 and Bs2 have the largest weight contents in the hydrophobic block and Bs1 has a lower molecular weight than Bs2 and Rs is an end-group which is H or a C1-O30 organic moiety;

wherein B1, B2, Bs1 and Bs2 are chosen from the group consisting of ε-caprolactone, δ-valerolactone, glycolide, lactide, 1,4-dioxan-2-one (also known as p-dioxanone) and 1,3-dioxan-2-one (also known as trimethylene carbonate), wherein the hydrophobic triblock copolymer (A) is fluid in a temperature range of 0° C. to 37° C. and wherein the weight % are relative to the sum of a), b) and c). Preferably R and Rs are independently chosen from the group consisting of H, acetyl, propionyl, butyryl, hexanoyl, dodecanoyl, and benzoyl.

In another embodiment the invention relates to a composition comprising:

a) 85-95.7 wt % of at least one type of hydrophobic triblock copolymer (A) of formula (1)

R—B-A-B—R     (1)

b) 0.3-5 wt % of at least one type of polymer surfactant (B) according to formula (2)

Rs-Bs-As-Bs-Rs     (2), and c) 4-10 wt % of water, wherein A is a hydrophilic block having an average molecular weight (Mn) of 100-1,000 Da, B is a hydrophobic block made from monomers comprising at least a monomer B1 and a monomer B2, wherein B1 and B2 have the largest weight contents in the hydrophobic block and B1 has a lower molecular weight than B2, wherein R is an end group which is H or a C1-C30 organic moiety;

wherein As is a hydrophilic block having an number average molecular weight (Mn) of at least 1,000 Da, Bs is a hydrophobic block made from monomers comprising at least a monomer Bs1 and a monomer Bs2 wherein Bs1 and Bs2 have the largest weight contents in the hydrophobic block and Bs1 has a lower molecular weight than Bs2 and Rs is an end-group which is H or a C1-C30 organic moiety;

wherein B1, B2, Bs1 and Bs2 are chosen from the group consisting of ε-caprolactone, δ-valerolactone, glycolide, lactide, 1,4-dioxan-2-one (also known as p-dioxanone) and 1,3-dioxan-2-one (also known as trimethylene carbonate), wherein the hydrophobic triblock copolymer (A) is fluid in a temperature range of 0° C. to 37° C. and wherein the weight % are relative to the sum of a), b) and c).

Preferably R and Rs are independently chosen from the group consisting of H, acetyl, propionyl, butyryl, hexanoyl, dodecanoyl, and benzoyl.

Pharmaceutical Composition.

Preferably, the composition according to the invention further comprises at least one active pharmaceutical ingredient (API). In this case, the composition according to the invention can be used as a pharmaceutical composition. The amount of the active pharmaceutical ingredient is preferably 0.01-15 wt %, relative to the total weight of the pharmaceutical composition.

Preferably the pharmaceutical composition comprises anyone of the compositions as defined above. It has been surprisingly found that the viscosity of the pharmaceutical composition is largely determined by the polymer emulsion, while the therapeutically active agent has only a minor effect on the injectability of the formulated composition. This is even independent of the molecular weight of the therapeutically active agent and the nature of the active pharmaceutical ingredient. Moreover, an advantage of the pharmaceutical composition of the present invention is that even hydrophilic active pharmaceutical ingredient, like for example lysozyme demonstrated a slow to very slow release.

An active pharmaceutical ingredient (API) or active pharmaceutical ingredients (API's), or also called therapeutically active agents or biologically active agents, people skilled in the art refer to any set of molecules, cells or cell materials able to prevent, slow down, moderate or cure a disease in, or that can deliver a desired therapeutic effect on, a treated human or animal. Human diseases are also referred to as defined by the World Health Organization in the WHO ICD-10 (2007) classification document.

The active pharmaceutical ingredient in the composition of the present invention may be an active ingredient such as any therapeutically active ingredient and any diagnostic and any contrast agent and includes those active pharmaceutical ingredients having a prophylactic effect on the animal, including human as well as those therapeutically active ingredients that have an effect of alleviating, reducing or even completely eliminating a symptom, or a cause, or a consequence of a disease, such as pain, swelling or inflammation or a disease from the animal, including human. For example, the active pharmaceutical ingredient may include broad classes of compounds normally delivered into the body. For example, these active pharmaceutical ingredients include but are not limited to anti-infectives (including antibiotics, antivirals, fungicides, scabicides or pediculicides); antiseptics (e.g. benzalkonium chloride, benzethonium chloride, chorhexidine gluconate, mafenide acetate, methylbenzethonium chloride, nitrofurazone, nitromersol and the like); analgesics and analgesic combinations; anorexics; antihelminthics, antiarthritics, antiasthmatic agents; anticonvulsants; antidepressants; antidiabetic agents; antidiarrheals; antihistamines; anti-inflammatory agents, antimigraine preparations; antinauseants; antineoplastics; antiparkinsonism drugs; antipuritics; antipsychotics; antipyretics, antispasmodics; anticholinergics; sympathomimetics; xanthine derivatives; cardiovascular preparations including potassium and calcium channel blockers; beta-blockers; alpha-blockers and antiarrhythmics; antihypertensives; diuretics and antidiuretics; vasodilators including general coronary, peripheral and cerebral vasodilators; central nervous system stimulants; vasoconstrictors; cough and cold preparations, including decongestants; hormones and steroids (e.g. estrogens, progestins, androgens, adrenocorticoids, corticosteroids and the like); hypnotics; immunosuppressives; muscle relaxants; parasympatholytics; psychostimulants; sedatives and tranquilizers, narcotics (e.g. morphine, meperidine, codeine and the like), local anesthetics (e.g. amide- or anilide-type local anesthetics such as bupivacaine, dibucaine, mepivacaine, procaine, lidocaine, tetracaine and the like); antiemetic agents (e.g. ondansetron, granisetron, tropisetron, metoclopramide, domperidone, scopolamide and the like); antiangiogenic agents (e.g. combrestatine, contortrostatin, anti-VEGF and the like), polysaccharides, immune-modulating, anti-thrombogenic compounds, anti-claudicating drugs, anti-antherosclerotic drugs, antihistamines, anti-cancer drugs (e.g. mechlorethamine, cyclophosphamide, fluorouracil, thioguanine, carmustine, lomustine, melphalan, chloambucil, streptozocin, methotrexate, vincristine, bleomycin, vinblastine, vindesine, dactinomycine, daunorubicin, doxorubicin, tamoxifen, paclitaxel, epirubicin, mitomicin C, cisplatin, carboplatin, and the like and photosensitizers used in photodynamic therapy, vascular drugs, ophthalmic drugs, amino acids, vitamins, neurotransmitters, neurohormones, signaling molecules, psychoactive medicaments, synthetic drugs, semi-synthetic drugs, natural drugs and substances derived from these, or combinations of the above.

The active pharmaceutical ingredient may also be a biological including but not limited to (recombinant) proteins, PEGylated-proteins and peptides (e.g. insulin, erythropoietin, exenatide, glucagon-like-peptide-1, morphogenic proteins (e.g. bone morphogenic proteins, transforming growth factors, fibroblast growth factors, tumor necrosis factors), receptor antagonists (e.g. Interleukin-1-receptor-antagonist), anticancer proteins (e.g. neocarzinostatin, L-asparaginase, interleukin-2, bevacizumab and other anti-VEGF agents) prophylactic vaccines, therapeutic vaccines, genetic materials (e.g. nucleic acid sequences, polynucleotides, (antisense) oligonucleotides, plasmids, DNA, RNA, siRNA, microRNA), aptamers, enzymes, antigens, antibodies, antibody fragments, viruses, virus-based materials, cells, cellular substructures, etc.), Prodrugs, metabolites, derivatives, in-vivo or in in-vitro chemically modified products, in-vivo or in-vitro enzymatic modified products and therapeutically active degradation products of the therapeutically active ingredients described herein are included in the scope of the invention.

Preferably, the active ingredient is a therapeutically active ingredient chosen from the group of immune-modifying drugs, anti-inflammatory drugs or growth factors.

Preferably, the active ingredient is a therapeutically active ingredient chosen from the group of immune-modifying drugs for example cyclosporine, tacrolimus (FK-506), sirolimus or rapamycin.

Preferably, the active ingredient is a therapeutically active ingredient chosen from the group of steroidal anti-inflammatory drugs, for example prednisone, prednisolon, triamcinolon, clobetasol or betamethason.

Preferably, the active ingredient is a therapeutically active ingredient chosen from the group of non-steroidal anti-inflammatory drugs, for example aspirin, diclofenac, piroxicam, meloxicam, ibuprofen or a selective COX-2 inhibitor for example celecoxib, valdecoxib, etoricoxib or rofecoxib.

Preferably, the active ingredient is a therapeutically active ingredient chosen from the group of anticancer agents for example bevacizumab, tamoxifen or interleukin-2.

Preferably, the active ingredient is a therapeutically active ingredient chosen from the group of anti-viral agents for example acyclovir or oseltamivir.

Preferably, the active ingredient is a therapeutically active ingredient chosen from the group of anti-bacterial agents for example amoxicillin.

Preferably, the active ingredient is a therapeutically active ingredient chosen from the group of anti-diabetic agents for example insulin, glucagon-like-peptide-1, and exenatide.

Preferably, the active ingredient is a therapeutically active ingredient chosen from the group of vaccines.

Preferably, the active ingredient is a therapeutically active ingredient chosen from the group of ophthalmic agents for example Triamcinolone and Bevacizumab.

Preferably, the active ingredient is a therapeutically active ingredient effective against forms of neuro-degenerative diseases such as apomorphine, rivastigmine, pramipexole, pioglitazone, memantine and safinamide Preferably, the active ingredient is a therapeutically active ingredient chosen from the group of biologicals including but not limited to growth factors which are very suitable for application in orthopedics and in particular in the prevention or treatment of diseases of intervertebral discs, or cartilage, or bone. Examples of such growth factors include but are not limited to transforming growth factor 3, fibroblast growth factor 18, osteogenic protein 1, bone morphogenic protein 2, bone morphogenic protein 6, bone morphogenic protein 7, interleukin-1-receptor-antagonist.

Preferably, the active ingredient belongs to the class of human growth hormones and its biosimilar derivatives, which can be applied in both pediatric and adult growth disorders, maintenance of sufficient musculature, and for anti-ageing applications.

Preferably, the active ingredient is a therapeutically active ingredient effective against inflammation or microbial infections of the inner ear and its connecting tissues, (intratympanic ear diseases).

Preferably, the active ingredient is a therapeutically active ingredient effective against forms of diabetes, for example insulin and glucagon-like-peptide-1, and their derivatives such as exendin-4 and liraglutide.

For the active ingredient which are water-soluble, the drug preferably has a solubility in water of at least 20 µg/ml, for example of at least 100 µg/ml, for example of at least 500 µg/ml, for example of at least 1,000 µg/ml, for example of at least 5,000 µg/ml in water measured at 20° C. and at atmospheric pressure (1 bar).

Examples of water-soluble active ingredients include small molecules (of up to 5,000 Da), medium sized molecules (of up to 10,000 Da), but also large molecules (of at least 10,000 Da), such as proteins. These water-soluble active agents may be synthesized chemically, but may also be a biological including but not limited to (recombinant) proteins and peptides (e.g. insulin, erythropoietin, exenatide, glucagon-like-peptide-1, morphogenic proteins (e.g. bone morphogenic proteins, transforming growth factors, fibroblast growth factors, tumor necrosis factors), receptor antagonists (e.g. interleukin-1-receptor-antagonist), anticancer proteins (e.g. neocarzinostatin, L-asparaginase, interleukin-2, bevacizumab and other anti-VEGF agents) prophylactic vaccines, therapeutic vaccines, genetic materials (e.g. nucleic acid sequences, polynucleotides, (antisense) oligonucleotides, plasmids, DNA, RNA, siRNA, microRNA), aptamers, enzymes, antigens, antibodies, antibody fragments, viruses, virus-based materials, cells, cellular substructures, etc.).

Therefore, the invention also relates to a composition according to the invention, wherein the active ingredient is a therapeutically active ingredient selected from the group of water-soluble drugs, that is drugs that have a solubility in water of at least 20 μg/ml as determined using the method described herein.

The invention also relates to a composition, wherein the composition further comprises nano-particles and/or microparticles (such as liposomes and microspheres) which particles contain any of the active pharmaceutical ingredients as described above.

Active pharmaceutical ingredients include but are not limited to nutrients, pharmaceuticals (small molecular entities), proteins and peptides, vaccines, genetic materials, (such as polynucleotides, oligonucleotides, plasmids, DNA and RNA), diagnostic agents, imaging agents, enzymes, nucleic acid sequences, antigens, antibodies, antibody fragments, viruses, virus-based materials, cells, cell substructures, growth factors, antibiotics, anti-inflammatory compounds, immune-modulating, anti-thrombogenic compounds, anti-claudicating drugs, anti-arrhythmic drugs, anti-atherosclerotic drugs, antihistamines, cancer drugs, vascular drugs, ophthalmic drugs, amino acids, vitamins, hormones, neurotransmitters, neurohormones, enzymes, signaling molecules, psychoactive medicaments, synthetic drugs, semi-synthetic drugs, natural drugs and substances derived from these, or combinations of the above.

An active pharmaceutical ingredient (API), may demonstrate any kind of activity, depending on the intended use. The active agent may be capable of stimulating, blocking or suppressing a biological response.

The active pharmaceutical ingredients can be used for sustained delivery in many different diseases and conditions within humans and animal.

Furthermore, the depot forming polymers will be completely resorb after having completed their function. This is especially important in the application in the area of intervertebral discs, where there is less metabolic activity.

In still another embodiment the active pharmaceutical ingredient is an agent to avoid, control, suppress, or eradicate infectious diseases.

An active pharmaceutical ingredient can be present in the polymer composition or emulsion in an amount of 0.01 to 15% by weight relative to the total weight of the composition or emulsion. Preferably, the active pharmaceutical ingredients are present in an amount of 0.02 to 10% by weight, more preferably in an amount of 0.05 to 8% by weight.

The invention also relates to a composition for use as a medicament, for use in therapy, surgery or in vivo diagnostics.

The invention is also directed to the use of the composition according to the invention or the pharmaceutical composition according to the invention for forming soft matter in an animal or human body after injection.

The invention is also directed to the use of the composition according to the invention or the pharmaceutical composition according to the invention for forming a depot in an animal or human body after injection.

The invention is also directed to the use of the composition according to the invention or the pharmaceutical composition according to the invention as medical device.

The invention also relates to a process for preparing a pharmaceutical composition, comprising the steps of mixing components a), b), c and an active pharmaceutical ingredient.

Tissue Engineering

Applications of tissue engineering devices comprising the composition according to the present invention include, but are not limited to, nerve growth or repair, cartilage growth or repair, bone growth or repair, muscle growth or repair, skin growth or repair, secreting gland repair, ophthalmic repair. It should be underlined that the soft matter may be used as such or as a part of a bigger implant, scaffold or structure.

The composition according to the invention may also be used as temporary void fillers in case of significant trauma, to prevent adhesion of damage tissues and scar tissue formation while dither or not waiting for corrective and reconstructive surgery. Void filling could be performed easily by injecting the composition according to the invention. Other benefits of using said composition according to the invention as void fillers may include but are not limited to: preventing contamination from outside, preventing infection, preventing surrounding tissue necrosis or alteration, inducing specific tissue formation (bone, cartilage, muscle, nerve, skin etc.), helping to maintain structural integrity of the surrounding tissues by itself or by combination with other known scaffolds or structures, trapping specific natural or foreign molecules.

The composition according to the invention may also be used as bioresorbable dermal fillers.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

BRIEF DESCRIPTION OF THE DRAWINGS

FIG. 1 shows the release of lidocaine-HCl from IVR formulations with a linear bioresorbable triblock copolymer and no surfactant (see experiment 4, comparative)

FIG. 2 shows an example of lysozyme release from formulations prepared with Pluronics 10R5 as surfactant (experiment 6)

FIG. 3 shows the release of lidocaine-HCL in the presence of Pluronics 17R4 as surfactant FIG. 4 shows the release profile of lidocaine-HCl from emulsions based on the hydrophobic triblock copolymer PEG200($cap_{75}$-$lac_{25}$)$_{4.0}$-C3.

FIG. 5 shows the release profile of lidocaine-HCl from emulsions based on the hydrophobic triblock copolymer PEG200(cap$_{50}$-lac$_{50}$)$_{5.0}$-C3.

FIG. 6 shows the release profile of lidocaine-HCl from emulsions based on the hydrophobic triblock copolymer PEG400(cap$_{50}$-lac$_{50}$)$_{3.0}$-C3.

FIG. 7 shows the release profile of lidocaine-HCl from emulsions based on the hydrophobic triblock copolymer PEG600(cap$_{50}$-lac$_{50}$)$_{2.0}$-C3 with different surfactants.

FIG. 8 shows the release of Lidocaine-HCl whereas also a commercially available surfactant is used (Pluronics 17R4) (66).

FIG. 9 illustrates the in vitro release of lysozyme from PEG600(cap$_{50}$-lac$_{50}$)$_{2.0}$-C3 formulations with and without a polymer surfactant.

FIG. 10 illustrates the effect of a surfactant for the formulations based on the hydrophobic triblock copolymer PEG200(cap$_{50}$-lac$_{50}$)$_{5.0}$-C3 and PEG400(cap$_{50}$-lac$_{50}$)$_{0.3.0}$-C3.

FIG. 11 shows the release profile of lysozyme from several different formulations.

FIG. 12 shows the effect of surfactants on the release of lysozyme (formulations 112, 113 and 114).

FIG. 13 shows the release of IgG of formulations 106 and 111.

FIG. 14 shows the release of lysozyme according to experiments 86 and 88.

FIG. 15 shows the IVR of formulation 115, directly after preparation and after 2 weeks of storage.

FIG. 16 shows the IVR of IgG from PEG600(cap$_{50}$-lac$_{50}$)$_{2.0}$-C3 formulations with two surfactants (B)

FIG. 17 shows the IVR of lysozyme from PEG600(cap$_{50}$-diox$_{50}$)$_{4.0}$-2-n-HD formulations with two surfactants (B).

FIG. 18 shows the IVR of hydrophobic triblock copolymer blends loaded with IgG.

FIG. 19 shows a depot of a pharmaceutical composition in rat cadaver (experiment 21).

DETAILED DESCRIPTION OF THE INVENTION

Examples

Materials:

Toluene, diethylether and n-pentane were purchased from Boom (Meppel, The Netherlands). ε-Caprolactone, triethylamine, acetic anhydride and propionic anhydride were purchased from Acros Organics (New Jersey, USA) and PEG200, PEG400, PEG600, PEG1000, PEG1500, hexanoic anhydride, Pluronics 17R4, Pluronics 10R5; Kolliphor P407, Kolliphor P188, PVP (40k) and tin(II)2-ethylhexanoate from Sigma Aldrich (St. Louis, USA). Lauric anhydride was purchased from ABCR (Karlsruhe, Germany). The API's lidocaine-HCl and lysozyme were purchased from Sigma Aldrich (St. Louis, USA). The monomers L-lactide, D-lactide and glycolide were purchased from Purac (Gorinchem, The Netherlands). p-Dioxanone was purchased from HBCChem, Inc. (USA). IgG was purchased from Sanquin (The Netherlands).

Test Methods

Molecular weights were determined by SEC using an Agilent system Series 100 equipped with a guard column (PLgel 5 µm, 7.5×50 mm) and three Varian columns (PLgel, 5 µm, 500 Å, 300×7.5 mm). Detection was performed with a refractive index detector. PEG standards of different molecular weights were used for reference. The eluent was THF, the elution rate was 1.0 ml/min. The column temperature was 35° C. The concentration of the samples was approx. 4 mg/ml in THF and the injection volume was 50 µl. $M_n$ polymer is the number average molecular weight of the polymer relative to the PEG standards and measured in THF.

Thermal properties of the polymers were determined by DSC (TA Instruments DSC 02000 apparatus). Samples of approximately 10 mg in closed Aluminium pans were cooled from room temperature to −90° C. and kept isothermal for 5 minutes, after which they were heated to 70° C. with a heating rate of 10° C./min (modulated +/−1° C. every 60 seconds). Next, the samples were cooled to −90° C. with a cooling rate of 5° C./min (modulated +/−1° C. every 60 seconds), followed by a second heating cycle to 70° C. with a heating rate of 2° C./min (modulated +/−1° C. every 60 seconds). Using the second heating run, the glass transition temperature ($T_g$) was determined as the midpoint of heat capacity change and the melting temperature ($T_m$) as the maximum temperature of the endothermic area.

Viscosity measurements were carried out on a TA Instruments AR2000Ex with a plate-cone setup, type 40 mm cone, angle 1:00:00 deg:min:sec. During the viscosity measurement, the temperature was kept constant at either 20° C. or 37° C., with a shear rate 5 s$^{-1}$ during 300 s. Average viscosity values were calculated using software (Trios software, TA Instruments). In this way the average dynamic (shear) viscosity of the polymer was determined.

Synthesis

General Synthesis Procedure Hydrophobic Triblock Copolymers:

In a three-neck round-bottom flask (500 ml) equipped with a Dean Stark trap and a condenser, PEG200 (20.6 g; 103 mmol), L-lactide (51.7 g; 359 mmol), ε-caprolactone (51.5 g; 452 mmol) and 250 ml toluene were introduced and, while stirring, heated to reflux under nitrogen atmosphere. The solution was azeotropically dried by distilling off 110 ml toluene/water. Next, it was cooled down to <90° C. and tin octoate (0.74 g; 1.8 mmol) was added. Ring-opening polymerization was carried out by refluxing the mixture overnight under nitrogen atmosphere. Subsequently, the solution was allowed to cool to room temperature.

Modification Procedures:

Modification with propionyl end-group; PEG200(cap$_{50}$-lac$_{50}$)$_{5.0}$-C3

To the reaction mixture, Et$_3$N (52.5 g; 515 mmol; 5 eq.) and propionic anhydride (40 g, 310 mmol, 3 eq.) were added. The resulting mixture was refluxed, while stirring, for 1 hour.

General Work-Up Procedure:

The reaction mixture was poured into a separation funnel containing n-pentane (600 ml). After shaking the mixture, the polymer settled to the bottom of the funnel and could be collected. The obtained polymer was dried under reduced pressure for 2 hours at 60° C., followed by further drying using a rotary evaporator (<0.2 mBar) at 90° C. for at least 48 hours.

Using this method as described above a library of polymers was prepared. Variations were made by using different PEG blocks, changing type of monomers used in the B-block and length of B block, and varying the endgroups. Results are listed in Table 1.

General Synthesis Procedure Polymer Surfactant (B):

In a three-neck round-bottom flask (500 ml) equipped with a Dean Stark trap and a condenser, PEG1500 (10 g; 6.7 mmol), L-lactide (11 g; 76 mmol), ε-caprolactone (11 g; 96 mmol) and 210 ml toluene were introduced and, while stirring, heated to reflux under nitrogen atmosphere. The solution was azeotropically dried by distilling off 110 ml toluene/water. Next, it was cooled down to <90° C. and tin octoate (0.2 g; 0.49 mmol) was added. Ring-opening polymerization was carried out by refluxing the mixture 36 hours under nitrogen atmosphere. Subsequently, the solution was allowed to cool to room temperature.

Modification Procedures:

Modification with acetyl end-group; PEG1500(cap$_{50}$-lac$_{50}$)$_{2.2}$-C2

To the reaction mixture, Et$_3$N (3.4 g; 33 mmol; 5 eq.) and acetic anhydride (2.0 g, 20 mmol, 3 eq.) were added. The resulting mixture was refluxed, while stirring, for 1 hour.

General Work-Up Procedure:

The reaction mixture was poured into a separation funnel containing n-pentane/diethylether (150/150 ml). After shaking the mixture, the polymer settled to the bottom of the funnel and could be collected. The obtained polymer was dried under reduced pressure for 2 hours at 60° C., followed by further drying using rotavap (<0.2 mBar) at 80° C. for at least 48 hours.

Using this method as described above a series of polymers was prepared. Variations were made by using different PEG blocks, changing type of monomers used in the Bs-block and length of Bs block, and varying the end-groups. Results are listed in Table 6.

Synthesis of a Diblockcopolymer (As-Bs-Rs) as Polymer Surfactant

MeO-PEG (mw=2000 g/mol; 6 g; 3 mmol), ε-caprolactone (4.8 g; 42 mmol), L-lactide (1.2 g; 8.3 mmol) and toluene (250 ml) were transferred into a three-neck round-bottom flask (500 ml). The flask was equipped with a Dean-Stark setup and water cooler. The mixture was stirred and heated till reflux, approx. 100 ml was collected with Dean-Stark and the resulting mixture was cooled down to room temperature, Tin octoate (0.033 g; 0.08 mmol) was added and the mixture was stirred and heated till reflux for 48 hours, followed by the addition of acetic anhydride (0.6 ml; 6.4 mmol) and Et$_3$N (1.2 ml; 4.3 mmol). The mixture was refluxed for 2 hours, cooled to room temperature and precipitated in n-pentane (750 ml). The polymer was collected and dried overnight at 80° C. under reduced pressure (<1 mBar).

Preparation of the Emulsions with Hydrophobic Bioresorbable Triblock Copolymer with/without a Polymer Surfactant and an API.

Preparation Formulation Method 1

A 10 wt % surfactant stock solution with API was prepared by dissolving the polymer surfactant (100 mg) and API (100 mg) in PBS (800 µl, 50 mM pH 7.4). The emulsion was prepared by mixing the hydrophobic bioresorbable triblock copolymer (1.8 g) with the surfactant/API stock solution (200 µl), using a spatula. Further mixing was done by using an Ultra-Turrax mixer at 12,000 rpm for 2 minutes. The final concentrations of surfactant and API were both 1 wt %.

Preparation Formulation Method 2

A mixture of hydrophobic bioresorbable triblock copolymer (1.8 g) and polymer surfactant (20 mg) was heated at 60° C. and allowed to stir at ambient temperature for one hour using a roller mixer. API stock solution (180 µl) in PBS (concentration 111 mg/ml, 50 mM, pH 7.4) was added and mixed using a spatula. The final emulsion was prepared by mixing using an Ultra-Turrax at 12,000 rpm for 2 minutes. The final concentrations of surfactant and API were both 1 wt %.

Preparation Formulation Method 3

A 10 wt % polymer surfactant stock solution with API was prepared by dissolving surfactant (100 mg) and API (100 mg) in PBS (800 µl, 50 mM pH 7.4). Finally the emulsion was prepared by mixing hydrophobic bioresorbable triblock copolymer (1.8 g) with the surfactant/API stock solution (200 µl), using a spatula. Further mixing was done by using a roller mixer overnight at ambient conditions. The final concentrations of surfactant and API were both 1 wt %.

Preparation Formulation Method 4

A 10 wt % stock solution with API was prepared by dissolving the API (100 mg) in PBS (900 µl, 50 mM pH 7.4). The hydrophobic bioresorbable triblock copolymer (1.8 g) was mixed with the API stock solution (200 µl), using a spatula. The final emulsion was prepared by mixing using the Ultra-Turrax at 12,000 rpm for 2 minutes. The final concentration API was 1 wt %.

Preparation Formulation Method 5 (Only for IgG)

A 20 wt % surfactant stock solution, Nanogam® (50 mg/ml IgG) and sometimes additional water were mixed for 2 hours at 4° C. using a roller mixer. A known amount was added to the hydrophobic bioresorbable triblock copolymer and mixed using a spatula. Further mixing was done by using the Ultra-Turrax at 12,000 rpm for 1 minute.

Preparation formulation method 6 (only for commercially available surfactants)

A 10 wt % surfactant solution was prepared by dissolving surfactant (100 mg) in PBS (900 µl, 50 mM pH 7.4). The emulsion was prepared by mixing hydrophobic bioresorbable triblock copolymer (1.8 g) with the surfactant solution (200 µl), using a spatula. The API (approx. 20 mg) was added, followed again by mixing with a spatula. Final mixing was done by using the Ultra-Turrax at 12,000 rpm for 2 minutes. The final concentrations of surfactant and API were both 1 wt %.

Preparation Formulation Method 7

A 20 wt % diblock solution in PBS was mixed with a lysozyme solution (40 mg/ml) in PBS, This lysozyme/diblock containing stock solution (0.2 g) was mixed with the hydrophobic bioresorbable triblock copolymer (1.8 g) using an Ultra-Turrax at 4,000 rpm for 1 minute, The final concentration was 0.2% lysozyme, 1% diblock and 9% PBS.

Preparation Formulation Method 8

Aqueous Phase:

First a 20 wt % ACEMIX was prepared by dissolving two polymer surfactants (PEG1500(cap$_{80}$-lac$_{20}$)$_{2.2}$-C2 (0.75 g) and PEG1500(cap$_{50}$-lac$_{50}$)$_{2.2}$-C2 (0.25 g)) in PB (4 ml).

To the ACEMIX (1.0 g) was added Nanogam (0.8 g; 50 mg/ml IgG) and PB (0.2 g). The solution was mixed on a rock-and-roller for 1 hour at 2-8° C. to obtain the final aqueous phase.

Blend Emulsion Formulations.

Two hydrophobic triblock copolymers (A) were weighted in a vial and mixed on a rock-and-roller for a couple hours at ambient temperature. Next a calculated amount of the prepared aqueous phase was added and mixed using a spatula followed by further mixing using the Ultra Turrax for 1 minute and 4,000 rpm at ambient temperature.

The resulting blend formulations were stored in the fridge (2-8° C.).

In Vitro Release (IVR) Setup

A known amount of formulation (approx. 200 mg) was transferred into glass tubes (15 ml), followed by the addition of 2 ml PBS (pH 7.4; 52 mM; 260 mOsm/kg; pre-warmed at 37° C.). The tubes were placed in a shaking incubator at 37° C.

Release samples were taken at various points in time. For sampling 1 ml of buffer was removed from the supernatant and replaced by pre-warmed PBS. The samples were analysed for its API content using reversed phase liquid chromatography.

Nomenclature

In the experimental section abbreviations for the hydrophobic bioresorbable triblock copolymer and polymer surfactant have been used.

For example PEG200(cap$_{50}$-lac$_{50}$)$_{5.0}$ means a triblock copolymer having an A-block made of PEG, having a number average molecular weight of 200 Da, and on each side of the A-block a B-block, wherein the total weight of the two B-blocks is equal to 5 times the molecular weight of the A-block, and wherein each B-block comprises ε-caprolactone and lactide in a 50/50 (weight) ratio. In this case the RBABR triblock copolymer comprises on average an A block consisting of PEG having Mn 200 Da, and two B blocks, each having a Mn of approximately 500 Da and containing 50 wt % ε-caprolactone and 50 wt % lactide. The end-group R is H in this case.

In cases where R is not H, the carbon chain length has been added to the formula.

For example PEG600(cap$_{50}$-lac$_{50}$)$_{2.0}$-C6 indicates a RBABR triblock copolymer having an A-block consisting of PEG having a number average molecular weight (Mn) of 600 Da, and two B-blocks each having a number average molecular weight (Mn) of approximately 600 Da (1200/2) and on each side a C6 R-group.

Experiment 1; Preparation of Hydrophobic Bioresorbable Triblock Copolymers.

A large number of RBABR bioresorbable triblock copolymers have beer prepared in accordance with the general synthesis procedure. Thermal properties and molecular weights have been determined. The results are listed in Table 1.

TABLE 1

Polymer properties

| # | Triblock copolymer (A) | $M_{n, PE}$ | PE/PEG | $m_1/m_2$ | Degree of modification | $M_{n, polymer}$ | PDI | $T_g$ (° C.) | $T_m$ (° C.) |
|---|---|---|---|---|---|---|---|---|---|
| 1 | PEG200(cap$_{50}$-lac$_{50}$)$_{5.0}$ | 1000 | 5.0 | 1 | — | 1337 | 1.27 | −45 | — |
| 2 | PEG200(cap$_{50}$-lac$_{50}$)$_{5.0}$-C3 | 1000 | 5.0 | 1 | 2 | 1453 | 1.23 | −45 | — |
| 3 | PEG200(cap$_{50}$-lac$_{50}$)$_{5.0}$-C6 | 1000 | 5.0 | 1 | 2 | 1518 | 1.23 | −51 | — |
| 4 | PEG200(cap$_{50}$-lac$_{50}$)$_{5.0}$-C12 | 1000 | 5.0 | 1 | 2 | 1570 | 1.23 | −53 | — |
| 5 | PEG200(cap$_{50}$-lac$_{50}$)$_{7.5}$ | 1500 | 7.5 | 1 | — | 1840 | 1.33 | −40 | — |
| 6 | PEG200(cap$_{50}$-lac$_{50}$)$_{7.5}$-C3 | 1500 | 7.5 | 1 | 2 | 1850 | 1.38 | −39 | — |
| 7 | PEG200(cap$_{50}$-lac$_{50}$)$_{7.5}$-C6 | 1500 | 7.5 | 1 | 2 | 1972 | 1.36 | −47 | — |
| 8 | PEG200(cap$_{50}$-lac$_{50}$)$_{10}$ | 2000 | 10 | 1 | — | 2659 | 1.37 | −37 | — |
| 9 | PEG200(cap$_{50}$-lac$_{50}$)$_{10}$-C3 | 2000 | 10 | 1 | 2 | 2275 | 1.50 | −36 | — |
| 10 | PEG200(cap$_{50}$-lac$_{50}$)$_{10}$-C6 | 2000 | 10 | 1 | 2 | 2493 | 1.44 | −40 | — |
| 11 | PEG600(cap$_{50}$-lac$_{50}$)$_{1.0}$ | 600 | 1.0 | 1 | — | 1206 | 1.10 | −57 | −5 |
| 12 | PEG600(cap$_{50}$-lac$_{50}$)$_{1.0}$-C3 | 600 | 1.0 | 1 | 2 | 1255 | 1.10 | −58 | −5 |
| 13 | PEG600(cap$_{50}$-lac$_{50}$)$_{1.0}$-C6 | 600 | 1.0 | 1 | 2 | 1387 | 1.09 | −63 | −8 |
| 14 | PEG600(cap$_{50}$-lac$_{50}$)$_{2.0}$ | 1200 | 2.0 | 1 | — | 1767 | 1.20 | −51 | — |
| 15 | PEG600(cap$_{50}$-lac$_{50}$)$_{2.0}$-C3 | 1200 | 2.0 | 1 | 2 | 1850 | 1.20 | −51 | — |
| 16 | PEG600(cap$_{50}$-lac$_{50}$)$_{2.0}$-C6 | 1200 | 2.0 | 1 | 2 | 1989 | 1.20 | −55 | — |
| 17 | PEG600(cap$_{50}$-lac$_{50}$)$_{4.0}$ | 2400 | 4.0 | 1 | — | 3254 | 1.32 | −40 | — |
| 18 | PEG600(cap$_{50}$-lac$_{50}$)$_{4.0}$-C3 | 2400 | 4.0 | 1 | 2 | 3432 | 1.31 | −40 | — |
| 19 | PEG600(cap$_{50}$-lac$_{50}$)$_{4.0}$-C6 | 2400 | 4.0 | 1 | 2 | 3182 | 1.36 | −45 | — |
| 20 | PEG1000(cap$_{50}$-lac$_{50}$)$_{0.5}$ | 500 | 0.5 | 1 | — | 1520 | 1.06 | −48 | 25 |
| 21 | PEG1000(cap$_{50}$-lac$_{50}$)$_{0.5}$-C3 | 500 | 0.5 | 1 | 2 | 1556 | 1.06 | −53 | 22 |
| 22 | PEG1000(cap$_{50}$-lac$_{50}$)$_{0.5}$-C6 | 500 | 0.5 | 1 | 2 | 1661 | 1.04 | −62 | 15 |
| 23 | PEG200(cap$_{75}$-lac$_{25}$)$_{5.0}$ | 1000 | 5.0 | 3 | — | 1422 | 1.26 | −62 | 1 |
| 24 | PEG200(cap$_{75}$-lac$_{25}$)$_{5.0}$-C3 | 1000 | 5.0 | 3 | 2 | 1487 | 1.27 | −61 | 1 |
| 25 | PEG200(cap$_{75}$-lac$_{25}$)$_{5.0}$-C6 | 1000 | 5.0 | 3 | 2 | 1688 | 1.24 | −66 | −8 |
| 26 | PEG200(cap$_{25}$-lac$_{75}$)$_{5.0}$ | 1000 | 5.0 | 1/3 | — | 1277 | 1.24 | −27 | — |
| 27 | PEG200(cap$_{25}$-lac$_{75}$)$_{5.0}$-C3 | 1000 | 5.0 | 1/3 | 2 | 1391 | 1.23 | −25 | — |
| 28 | PEG200(cap$_{25}$-lac$_{75}$)$_{5.0}$-C6 | 1000 | 5.0 | 1/3 | 2 | 1514 | 1.20 | −30 | — |
| 29 | PEG200(cap$_{75}$-lac$_{25}$)$_{7.5}$-C3 | 1500 | 7.5 | 3 | 2 | 1847 | 1.40 | N.A. | N.A. |
| 30 | PEG200(cap$_{75}$-lac$_{25}$)$_{7.5}$-C6 | 1500 | 7.5 | 3 | 2 | 2081 | 1.34 | N.A. | N.A. |
| 31 | PEG200(cap$_{50}$-diox$_{50}$)$_{5.0}$ | 1000 | 5.0 | 1 | — | 1300 | 1.22 | −60 | — |
| 32 | PEG200(cap$_{50}$-diox$_{50}$)$_{5.0}$-C3 | 1000 | 5.0 | 1 | 2 | 1273 | 1.23 | −58 | — |
| 33 | PEG200(cap$_{50}$-diox$_{50}$)$_{5.0}$-C6 | 1000 | 5.0 | 1 | 2 | 1245 | 1.17 | −73 | −4 |

In Table 1 PEG200, PEG400, PEG600 and PEG1000 are polyethylene glycol polymers with a number average molecular weight of respectively 200 Da, 400 Da, 600 Da and 1,000 Da.

$M_{n,\ PE}$: the number average molecular weight of both B-blocks together, as calculated based on the molecular weight of the A-block.

Cap is an abbreviation for ε-caprolactone.

Lac is an abbreviation for L-lactide, D-Lactide or DL-Lactide If not specifically mentioned, L-Lactide is chosen by default.

Diox is an abbreviation of p-dioxanone

C6 and C12 mean that the R-group comprises respectively 3 (propionyl), 6 (hexanoyl) or 12 (lauroyl) carbon atoms.

PE/PEG: the weight ratio of polyester to PEG (B/A) or (Bs/As)

$m_1/m_2$: the ratio of the first monomer to the second monomer in the B block

Degree of modification: stands for number of aliphatic end-groups (R) after polymer modification. When the degree of modification is indicated as --, it means that R=H in the formula RBABR. When the degree of modification is 2, it means that R is a fatty acid residue comprising a number of C atoms.

$M_{n,\ polymer}$: number average molecular weight of the polymer as determined with GPC PDI: polydispersity index according to GPC $T_g$: glass transition temperature (midpoint) according to DSC $T_m$: melting temperature according to DSC N.A.: not analyzed Experiment 2; Viscosity Measurements Polymers The viscosity of the polymers listed in Table 1 have been measured at 20° C. and 37° C. Results are listed in Table 2.

TABLE 2

Results rheology experiments

| # | Triblock copolymer (A) | Viscosity Pa · s At 20° C. | At 37° C. |
|---|---|---|---|
| 1 | PEG200(cap$_{50}$-lac$_{50}$)$_{5.0}$ | 7.6 | 1.6 |
| 2 | PEG200(cap$_{50}$-lac$_{50}$)$_{5.0}$-C3 | 6.2 | 1.2 |
| 3 | PEG200(cap$_{50}$-lac$_{50}$)$_{5.0}$-C6 | 4.8 | 1.1 |
| 4 | PEG200(cap$_{50}$-lac$_{50}$)$_{5.0}$-C12 | 4.0 | 1.0 |
| 5 | PEG200(cap$_{50}$-lac$_{50}$)$_{7.5}$ | 19 | 3.0 |
| 6 | PEG200(cap$_{50}$-lac$_{50}$)$_{7.5}$-C3 | 16 | 3.2 |
| 7 | PEG200(cap$_{50}$-lac$_{50}$)$_{7.5}$-C6 | 7.3 | 2.4 |
| 8 | PEG200(cap$_{50}$-lac$_{50}$)$_{10}$ | 60 | 9.8 |
| 9 | PEG200(cap$_{50}$-lac$_{50}$)$_{10}$-C3 | 53 | 8.8 |
| 10 | PEG200(cap$_{50}$-lac$_{50}$)$_{10}$-C6 | 36 | 7.4 |
| 11 | PEG600(cap$_{50}$-lac$_{50}$)$_{1.0}$ | 1.3 | 0.4 |
| 12 | PEG600(cap$_{50}$-lac$_{50}$)$_{1.0}$-C3 | 0.9 | 0.3 |
| 13 | PEG600(cap$_{50}$-lac$_{50}$)$_{1.0}$-C6 | 0.5 | 0.3 |
| 14 | PEG600(cap$_{50}$-lac$_{50}$)$_{2.0}$ | 6.3 | 1.4 |
| 15 | PEG600(cap$_{50}$-lac$_{50}$)$_{2.0}$-C3 | 5.1 | 1.3 |
| 16 | PEG600(cap$_{50}$-lac$_{50}$)$_{2.0}$-C6 | 3.9 | 1.1 |
| 17 | PEG600(cap$_{50}$-lac$_{50}$)$_{4.0}$ | 56 | 10.3 |
| 18 | PEG600(cap$_{50}$-lac$_{50}$)$_{4.0}$-C3 | 36 | 9.2 |
| 19 | PEG600(cap$_{50}$-lac$_{50}$)$_{4.0}$-C6 | 33 | 7.2 |
| 20 | PEG1000(cap$_{50}$-lac$_{50}$)$_{0.5}$ | 117 | 0.4 |
| 21 | PEG1000(cap$_{50}$-lac$_{50}$)$_{0.5}$-C3 | 2.0 | 0.3 |
| 22 | PEG1000(cap$_{50}$-lac$_{50}$)$_{0.5}$-C6 | 3.2 | 0.3 |
| 23 | PEG200(cap$_{75}$-lac$_{25}$)$_{5.0}$ | 1.9 | 0.6 |
| 24 | PEG200(cap$_{75}$-lac$_{25}$)$_{5.0}$-C3 | 1.8 | 0.6 |
| 25 | PEG200(cap$_{75}$-lac$_{25}$)$_{5.0}$-C6 | 1.6 | 0.4 |
| 26 | PEG200(cap$_{25}$-lac$_{75}$)$_{5.0}$ | 92 | 7.7 |
| 27 | PEG200(cap$_{25}$-lac$_{75}$)$_{5.0}$-C3 | 61 | 6.6 |
| 28 | PEG200(cap$_{25}$-lac$_{75}$)$_{5.0}$-C6 | 38 | 5.0 |
| 29 | PEG200(cap$_{75}$-lac$_{25}$)$_{7.5}$-C3 | 4.3 | N.A. |
| 30 | PEG200(cap$_{75}$-lac$_{25}$)$_{7.5}$-C6 | 2.8 | N.A. |
| 31 | PEG200(cap$_{50}$-diox$_{50}$)$_{5.0}$ | 2.1 | 0.63 |
| 32 | PEG200(cap$_{50}$-diox$_{50}$)$_{5.0}$-C3 | 2.1 | 0.62 |
| 33 | PEG200(cap$_{50}$-diox$_{50}$)$_{5.0}$-C6 | 0.62 | 0.23 |

As shown in Table 2, the end-group (C3, C6 or C12) had a significant effect on the viscosity. In general, polymers with end-group R=H show a relatively high viscosity. C3-endcapped polymers had lower viscosities and C6 modified polymers had the lowest viscosity, compared to unmodified ones (with R=H).

The composition of the B-block is also of great importance. For example: a polymer with a composition of PEG200(cap$_{25}$-lac$_{75}$)$_{5.0}$-C3 has a high viscosity, while changing the composition to PEG200(cap$_{75}$-lac$_{25}$)$_{5.0}$-C3 resulted in a very low viscous polymer. The lowest viscosities were obtained when ε-caprolactone is the major component of the PE-block. The inventors believe that this has to do with the lower $T_g$ of ε-caprolactone monomer units compared to the more rigid lactate monomer units. Increasing the temperature to 37° C. results in less viscous polymers.

As shown in Table 1 polymers composed with PEG1000 have a melting temperature around 20° C. These polymers crystallize in the refrigerator (4° C.) and even at ambient temperature. End-capping these polymers lowers the melting temperature, but not low enough to prevent crystallization. However, the copolymers may be warmed up to 37° C. prior to injection to 'melt' the crystalline domains of the PEG. If preferred, said copolymers may be cooled to room temperature again prior to injection without immediate crystallization happens and without immediate increase in viscosity.

Experiment 3 (Comparative): Formulations of Hydrophobic Bioresorbable Triblock Copolymers with Water.

Hydrophilic API's are poorly soluble in the hydrophobic bioresorbable triblock copolymer alone. To improve the solubility, water was added to the hydrophobic triblock polymer. The emulsions were prepared with 10 wt % water according to preparation method 4.

TABLE 3

Formulations with water and API

| Formulation # | Preparation method # | hydrophobic triblock copolymer | 1 wt % API |
|---|---|---|---|
| 62 | 4 | PEG200(cap$_{50}$-lac$_{50}$)$_{5.0}$-C3 | Lidocaine-HCL |
| 63 | 4 | PEG400(cap$_{50}$-lac$_{50}$)$_{3.0}$-C3 | |
| 64 | 4 | PEG600(cap$_{50}$-lac$_{50}$)$_{2.0}$-C3 | |
| 65 | 4 | PEG200(cap$_{75}$-lac$_{25}$)$_{4.0}$-C3 | |
| 75 | 4 | PEG200(cap$_{50}$-lac$_{50}$)$_{5.0}$-C3 | Lysozyme |
| 76 | 4 | PEG400(cap$_{50}$-lac$_{50}$)$_{3.0}$-C3 | |
| 77 | 4 | PEG600(cap$_{50}$-lac$_{50}$)$_{2.0}$-C3 | |
| 76 | 4 | PEG1000(cap$_{75}$-lac$_{25}$)$_{0.5}$-C3 | |

In the presence of water the API's readily dissolved in the hydrophobic bioresorbable triblock copolymer and white formulations were obtained. Immediately after mixing, a part of the emulsions were used in an in vitro release (IVR)-study. Another part of the emulsions were stored in the fridge (2-8° C.). However, after approx. 24 hours, all the emulsions stored in the fridge were phase-separated in a water layer (on top) and a polymer layer.

TABLE 4

Viscosity of the prepared formulations

| Formulation # | Preparation method # | Viscosity (Pa · s) At 20° C. | At 37° C. |
|---|---|---|---|
| 62 | 4 | 2.3 | 0.52 |
| 63 | 4 | 3.3 | 0.73 |
| 64 | 4 | 2.1 | 0.57 |
| 65 | 4 | 0.68 | 0.22 |
| 75 | 4 | 2.8 | 1.0 |
| 76 | 4 | 0.96 | 0.20 |
| 77 | 4 | 2.0 | 0.52 |
| 78 | 4 | 0.33 | 0.14 |

All formulations had a much lower viscosity than the hydrophobic bioresorbable triblock copolymer (A) alone.

Experiment 4 (Comparative): IVR Formulations of Linear Hydrophobic Triblock Copolymer with Water Formulations as prepared in experiment 3 (see also table 3 and 4) have been tested for release of lidocaine-HCl. As shown in FIG. 1 the release of lidocaine-HCl was very fast with a high burst of 60% in the first 24 hours. Also the release of lysozyme was fast with a cumulative release of approx. 43% after 4 days.

Conclusion

Hydrophilic API are poorly soluble in the linear hydrophobic triblock copolymer alone. This can be circumvented by the addition of water. However, when only water is mixed with the hydrophobic triblock copolymer, unstable emulsions are formed. Meaning that, within 24 hours after preparing the emulsions, a water layer can be seen on top of the formulation. As a result the release of API from these emulsions is relatively fast.

Experiment 5 (Comparative): Preparation of Formulations with Surfactants Loaded with 1 wt % Lysozyme or Lidocaine-HCl To stabilize the emulsion and preventing the water to separate in a layer from the formulation, commercially available surfactants were used. Formulations were prepared according to preparation method 6 using PEG600(cap$_{50}$-lac$_{50}$)$_{2.0}$-C3 as hydrophobic triblock copolymer. An overview of the various surfactants is give in Table 5.

TABLE 5

Set of formulations with commercially available surfactants, including viscosity measurements

| Formulation** # | Surfactant | Viscosity (Pa · s) 20° C. | 37° C. | API |
|---|---|---|---|---|
| 66 | 1% Pluronics 17R4 | 3.4 | 0.93 | Lidocaine-HCl |
| 89 | 2% Pluronics 17R4 | 2.3 | 1.6 | Lysozyme |
| 90 | 1% Pluronics 17R4 | 2.1 | 0.57 | Lysozyme |
| 91 | 0.5% Pluronics 17R4 | 2.3 | 0.62 | Lysozyme |
| 92 | 2% Kolliphor P407 | 3.7* | 1.7* | Lysozyme |
| 93 | 1% Kolliphor P407 | 2.9* | 1.1* | Lysozyme |
| 94 | 0.5% Kolliphor P407 | 2.5* | 0.65* | Lysozyme |
| 95 | 2% Pluronics 10R5 | 2.5 | 0.66 | Lysozyme |

TABLE 5-continued

Set of formulations with commercially available surfactants, including viscosity measurements

| Formulation** # | Surfactant | Viscosity (Pa · s) 20° C. | 37° C. | API |
|---|---|---|---|---|
| 96 | 1% Pluronics 10R5 | 2.3 | 0.61 | Lysozyme |
| 97 | 0.5% Pluronics 10R5 | 1.9 | 0.52 | Lysozyme |
| 98 | 2% Kolliphor P188 | 2.6 | 0.71 | Lysozyme |
| 99 | 1% Kolliphor P188 | 2.3 | 0.64 | Lysozyme |
| 100 | 0.5% Kolliphor P188 | 2.1 | 0.56 | Lysozyme |
| 101 | 2% PVP | 2.7 | 0.73 | Lysozyme |
| 102 | 1% PVP | 2.2 | 0.61 | Lysozyme |
| 103 | 0.5% PVP | 2.2 | 0.62 | Lysozyme |

*Viscosity was not stable during the entire measurement.
**All formulations were based on the hydrophobic triblock copolymer PEG600(cap$_{50}$-lac$_{50}$)$_{2.0}$-C3 and prepared using method 6.

In the presence of water and surfactant the API's completely dissolved in the hydrophobic bioresorbable triblock copolymer and white formulations were obtained. Directly after mixing, the formulations were subjected to an in vitro release (IVR)-study.

Experiment 6 (Comparative): IVR of Formulations with Surfactants Loaded with 1 wt % Lysozyme FIG. 2 gives an example of lysozyme release from formulations prepared with Pluronics 10R5 as surfactant. The release during the first 3 days is 50-60%, not much retention was observed using this Pluronics 10R5 as surfactant. Not depicted in a Figure, but all the other formulations prepared with commercially available surfactants gave almost identical release profiles. In all cases 40-70% of lysozyme was released during the first 3 days. When stored in the fridge (2-8° C.), the formulations appeared stable for at least 24 hours.

Experiment 7 (Comparative): IVR of Formulations with Surfactants Loaded with 1 wt % Lidocaine-HCl As shown previously in FIG. 1, formulation 64 gives a very high burst in the first 24 hours. The addition of Pluronics 17R4 (formulation 66) as surfactant, resulted in a slightly lower burst release in the first 24 hours (FIG. 3).

In Conclusion

The use of the commercially available surfactants, as depicted in Table 5, did not result in a prolonged release of lysozyme. Although the emulsions obtained were stable for at least 24 hours, the addition of the commercially available surfactants did not result in (much) more retention of the API.

Experiment 8: Synthesis of Polymer Surfactants

Tailor-made surfactants (indicated as polymer surfactants) were prepared as depicted in Table 6. A set of polymer surfactants was prepared in accordance with the general synthesis procedure. Thermal properties and molecular weights have been determined and are listed in table 6.

TABLE 6

Synthesis linear polymer surfactant (B)

| # | Surfactant composition (B) | $M_{n, PE}$ | PE/PEG | m1/m2 | Degree of modification | $M_{n, polymer}$ | PDI | $T_g$ (°C.) | $T_m$ (°C.) |
|---|---|---|---|---|---|---|---|---|---|
| 34 | PEG1000($cap_{50}$-$lac_{50}$)$_{2.0}$-C2 | 2000 | 2.0 | 1 | 2 | 2735 | 1.42 | −60.4 | 15.3 |
| 35 | PEG1000($cap_{80}$-$lac_{20}$)$_{2.0}$-C2 | 2000 | 2.0 | 4 | 2 | 2630 | 1.30 | −46.2 | 13.3 |
| 36 | PEG1500($cap_{50}$-$lac_{50}$)$_{2.2}$-C2 | 3300 | 2.2 | 1 | 2 | 4450 | 1.38 | −46.5 | 15.1 |
| 37 | PEG1500($cap_{80}$-$lac_{20}$)$_{2.2}$-C2 | 3300 | 2.2 | 4 | 2 | 4605 | 1.50 | −56.9 | 23.0 |
| 38 | PEG1500($cap_{80}$-$lac_{20}$)$_{1.8}$-C3 | 2700 | 1.8 | 4 | 2 | 4424 | 1.35 | −56.3 | 21.6 |
| 39 | PEG2000($cap_{50}$-$lac_{50}$)$_{1.6}$-C2 | 3200 | 1.6 | 1 | 2 | 5128 | 1.32 | −48.1 | 27.5 |
| 40 | PEG2000($cap_{80}$-$lac_{20}$)$_{1.6}$-C2 | 3200 | 1.6 | 4 | 2 | 5190 | 1.35 | −54.6 | 32.9 |
| 41 | PEG1500($cap_{50}$-$diox_{50}$)$_{1.8}$-C2 | 2700 | 1.8 | 1 | 2 | 2884 | 1.28 | −63.0 | 31.5 |
| 42 | PEG1500($cap_{80}$-$diox_{20}$)$_{1.8}$-C2 | 2700 | 1.8 | 4 | 2 | 3825 | 1.42 | N.A. | N.A. |
| 43 | PEG1500($cap_{70}$-$lac_{30}$)$_{2.2}$-C2 | 3300 | 2.2 | 2.3 | 2 | N.A. | N.A. | −55.9 | 18.1 |
| 44 | PEG1500($cap_{60}$-$lac_{40}$)$_{2.2}$-C2 | 3300 | 2.2 | 1.5 | 2 | N.A. | N.A. | −49.5 | 20.2 |
| 45 | PEG1500($cap_{80}$-$lac_{20}$)$_{2.0}$-C2 | 3000 | 2.0 | 4 | 2 | N.A. | N.A. | −54.7 | 21.2 |
| 46 | PEG1500($cap_{80}$-$lac_{20}$)$_{1.8}$-C2 | 2700 | 1.8 | 4 | 2 | N.A. | N.A. | −56.3 | 21.3 |

The obtained polymer surfactants (B) are highly viscous, semi-solid polymers at room temperature. All surfactants have a low Tg value, mainly caused by the large amount of caprolactone present. Also all of these surfactants have a melting point, which is a contribution of the PEG-block. Although not presented in the table, all surfactants with a melting point show a crystallisation temperature.

Experiment 9: Preparation of Formulations Loaded with 1 wt % Lidocaine-HCl

TABLE 7 formulations loaded with 1 wt % lidocaine-HCl

| Formulation # | Preparation method # | hydrophobic triblock copolymer (A) | polymer surfactant (B) (1 wt %) |
|---|---|---|---|
| 47 | 2 | PEG200($cap_{75}$-$lac_{25}$)$_{4.0}$-C3 | PEG1500($cap_{80}$-$lac_{20}$)$_{2.2}$-C2 |
| 48 | 1 | PEG200($cap_{50}$-$lac_{50}$)$_{5.0}$-C3 | PEG1500($cap_{80}$-$lac_{20}$)$_{2.2}$-C2 |
| 49 | 2 | PEG200($cap_{50}$-$lac_{50}$)$_{5.0}$-C3 | PEG1500($cap_{80}$-$lac_{20}$)$_{2.2}$-C2 |
| 50 | 1 | PEG400($cap_{50}$-$lac_{50}$)$_{3.0}$-C3 | PEG1500($cap_{80}$-$lac_{20}$)$_{2.2}$-C2 |
| 51 | 2 | PEG400($cap_{50}$-$lac_{50}$)$_{3.0}$-C3 | PEG1500($cap_{80}$-$lac_{20}$)$_{2.2}$-C2 |
| 52 | 1 | PEG600($cap_{50}$-$lac_{50}$)$_{2.0}$-C3 | PEG1500($cap_{80}$-$lac_{20}$)$_{2.2}$-C2 |
| 53 | 2 | PEG600($cap_{50}$-$lac_{50}$)$_{2.0}$-C3 | PEG1500($cap_{80}$-$lac_{20}$)$_{2.2}$-C2 |
| 54 | 1 | PEG200($cap_{50}$-$lac_{50}$)$_{5.0}$-C3 | PEG1500($cap_{50}$-$lac_{50}$)$_{2.2}$-C2 |
| 55 | 2 | PEG200($cap_{50}$-$lac_{50}$)$_{5.0}$-C3 | PEG1500($cap_{50}$-$lac_{50}$)$_{2.2}$-C2 |
| 56 | 1 | PEG400($cap_{50}$-$lac_{50}$)$_{3.0}$-C3 | PEG1500($cap_{50}$-$lac_{50}$)$_{2.2}$-C2 |
| 57 | 2 | PEG400($cap_{50}$-$lac_{50}$)$_{3.0}$-C3 | PEG1500($cap_{50}$-$lac_{50}$)$_{2.2}$-C2 |
| 58 | 1 | PEG600($cap_{50}$-$lac_{50}$)$_{2.0}$-C3 | PEG1500($cap_{50}$-$lac_{50}$)$_{2.2}$-C2 |
| 59 | 2 | PEG600($cap_{50}$-$lac_{50}$)$_{2.0}$-C3 | PEG1500($cap_{50}$-$lac_{50}$)$_{2.2}$-C2 |
| 60 | 1 | PEG200($cap_{75}$-$lac_{25}$)$_{4.0}$-C3 | PEG1500($cap_{50}$-$lac_{50}$)$_{2.2}$-C2 |
| 61 | 2 | PEG200($cap_{75}$-$lac_{25}$)$_{4.0}$-C3 | PEG1500($cap_{50}$-$lac_{50}$)$_{2.2}$-C2 |

A series of hydrophobic triblock copolymers were mixed with water and a polymer surfactant (Table 7). After mixing with an Ultra-Turrax all the formulations were completely white and non-transparent. After a few hours the formulations containing the hydrophobic triblock copolymers with PEG600 (formulation 52, 53, 58 and 59) turned colourless and transparent; also no lidocaine-HCl particles were observed by optical microscopy. No separated water layers were seen, by eye, after storage in the fridge (2-9° C.) for 24 hours.

Experiment 10: Viscosity Measurements Formulations with 1 wt % Lidocaine-HCl

TABLE 8

Viscosity of the prepared formulations with 1 wt % lidocaine-HCl

| Formulation # | Preparation method # | Viscosity (Pa · s) At 20° C. | At 37° C. |
|---|---|---|---|
| PEG200($cap_{75}$-$lac_{25}$)$_{4.0}$-C3 | | 0.94 | 0.33 |
| 47 | 2 | 0.51 | 0.16 |
| 60 | 1 | 0.46 | 0.13 |
| 61 | 2 | 0.60 | 0.19 |
| PEG200($cap_{50}$-$lac_{50}$)$_{5.0}$-C3 | | 5.9 | 1.3 |
| 48 | 1 | 2.1 | 0.45 |
| 49 | 2 | 2.1 | 0.44 |
| 54 | 1 | 1.7 | 0.39 |
| 55 | 2 | 2.2 | 0.52 |
| PEG400($cap_{50}$-$lac_{50}$)$_{3.0}$-C3 | | 7.8 | 1.7 |
| 50 | 1 | 2.6 | 0.57 |
| 51 | 2 | 2.8 | 0.61 |
| 56 | 1 | 2.3 | 0.47 |
| 57 | 2 | 3.1 | 0.66 |
| PEG600($cap_{50}$-$lac_{50}$)$_{2.0}$-C3 | | 5.1 | 1.3 |
| 52 | 1 | 1.6 | 0.43 |
| 53 | 2 | 1.2 | 0.33 |
| 58 | 1 | 1.2 | 0.32 |
| 59 | 2 | 1.1 | 0.29 |

All prepared formulations had a much lower viscosity than the hydrophobic triblock copolymer alone. The viscosity of the formulations was reduced with more than 50%, which makes them more suitable for injection. Furthermore, there were no significant differences between the formulation prepared by preparation method 1 or 2.

Experiment 11: In Vitro Release Formulations Loaded with 1 wt % Lidocaine-HCl (Table 7 and Table 8).

FIG. 4 shows the release profile of lidocaine from emulsions based on the hydrophobic triblock copolymer PEG200 ($cap_{75}$-$lac_{25}$)$_{4.0}$-C3. As shown in FIG. 4 there are no significant differences in the lidocaine release profile for the three formulations. According to these results it doesn't make a difference which method is used to prepare the formulations. All three formulations showed a burst release of 35-45% after 1 day, followed by a slower release. After 1 week approx. 55% of the lidocaine was released. Also the choice of polymer surfactant (B) had no major effect on the release profile.

FIG. 5 shows the release profile of lidocaine from emulsions based on the hydrophobic triblock copolymer PEG200 ($cap_{50}$-$lac_{50}$)$_{5.0}$-C3. Again there is no significant difference in release profile between the formulation prepared by method 1 or method 2. The release is much slower than the formulations based on the hydrophobic triblock copolymer PEG200(cap$_{75}$-lac$_{25}$)$_{4.0}$-C3. After 24 hours only 10% was released and continued slowly to approx. 20% after 7 days. The addition of the polymer surfactant (B) had a significant effect on the long-term release. Formulation 62 is prepared without surfactant and shows a much faster release.

FIG. 6 shows the release profile of lidocaine from emulsions based on the hydrophobic triblock copolymer PEG400 (cap$_{50}$-lac$_{50}$)$_{3.0}$-C3. As shown in FIG. 6, the four different formulations have a similar release pattern. According to these results it doesn't make a difference which method was used to prepare the formulations. The four formulations show almost no burst release. After 1 day approx. 10% was released, which slowly continued to 25-30% of lidocaine release after 1 week.

FIG. 7 shows the release profile of lidocaine from emulsions based on the hydrophobic triblock copolymer PEG600 (cap$_{50}$-lac$_{50}$)$_{2.0}$-C3 with different surfactants. FIG. 7 illustrates again there is no significant difference which method (1 or 2) is used to prepare the formulations. Formulation 64 has no surfactant, which results in a much higher release of 60% after 1 day compared to about 30% for the other four formulations.

FIG. 8 shows the release of Lidocaine-HCl whereas also a commercially available surfactant is used (Pluronics 17R4) (66). The usage of Pluronics 17R4 gives a high burst of 50% in the first 24 hours. The polymer surfactant reduces the burst to a release of 30% in the first 24 hours.

Experiment 12: Preparation of Formulations Loaded with 1 wt % Lysozyme

A series of hydrophobic triblock copolymers were mixed with water, a polymer surfactant and lysozyme.

TABLE 9

Preparation formulations loaded with 1% lysozyme, using different methods

| Formulation # | Preparation method # | hydrophobic triblock copolymer (A) | polymer surfactant (B) (1 wt %) |
|---|---|---|---|
| 67 | 1 | PEG200(cap$_{50}$-lac$_{50}$)$_{5.0}$-C3 | PEG1500(cap$_{50}$-lac$_{50}$)$_{2.2}$-C2 |
| 68 | 2 | PEG200(cap$_{50}$-lac$_{50}$)$_{5.0}$-C3 | PEG1500(cap$_{50}$-lac$_{50}$)$_{2.2}$-C2 |
| 69 | 1 | PEG400(cap$_{50}$-lac$_{50}$)$_{3.0}$-C3 | PEG1500(cap$_{50}$-lac$_{50}$)$_{2.2}$-C2 |
| 70 | 2 | PEG400(cap$_{50}$-lac$_{50}$)$_{3.0}$-C3 | PEG1500(cap$_{50}$-lac$_{50}$)$_{2.2}$-C2 |
| 71 | 1 | PEG600(cap$_{50}$-lac$_{50}$)$_{2.0}$-C3 | PEG1500(cap$_{50}$-lac$_{50}$)$_{2.2}$-C2 |
| 72 | 2 | PEG600(cap$_{50}$-lac$_{50}$)$_{2.0}$-C3 | PEG1500(cap$_{50}$-lac$_{50}$)$_{2.2}$-C2 |
| 73 | 1 | PEG1000(cap$_{75}$-lac$_{25}$)$_{0.5}$-C3 | PEG1500(cap$_{50}$-lac$_{50}$)$_{2.2}$-C2 |
| 74 | 2 | PEG1000(cap$_{75}$-lac$_{25}$)$_{0.5}$-C3 | PEG1500(cap$_{50}$-lac$_{50}$)$_{2.2}$-C2 |
| 79 | 1 | PEG600(cap$_{50}$-lac$_{50}$)$_{2.0}$-C3 | PEG1500(cap$_{80}$-lac$_{20}$)$_{2.2}$-C2 |
| 80 | 1 | PEG600(cap$_{50}$-lac$_{50}$)$_{2.0}$-C3 | PEG1500(cap$_{50}$-lac$_{50}$)$_{2.2}$-C2 |
| 81 | 1 | PEG600(cap$_{50}$-lac$_{50}$)$_{2.0}$-C3 | PEG1500(cap$_{80}$-lac$_{20}$)$_{1.8}$-C3 |
| 82 | | Only hydrophobic triblock copolymer PEG600(cap$_{50}$-lac$_{50}$)$_{2.0}$-C3 | |
| 83 | | Hydrogel PEG1500(cap$_{80}$-lac$_{20}$)$_{1.8}$-C3 (20% in PBS) | |
| 84 | 1 | PEG600(cap$_{50}$-lac$_{50}$)$_{2.0}$-C3 | Pluronics 17R4 |

All the formulations were prepared successfully. Formulation 82 is the pure triblock copolymer mixed with lysozyme. Formulation 83 is a thermoresponsive hydrogel, for which a 20 wt % polymer solution in buffer was prepared. The solution, so obtained, is liquid in the fridge, but becomes a hydrogel when heated to 30° C. Lysozyme can dissolve easily in this formulation.

Experiment 13: Viscosity Measurements Formulations with 1 wt % Lysozyme

TABLE 10

Viscosity of prepared formulations with 1% lysozyme

| Formulation # | Preparation method # | Viscosity (Pa · s) At 20° C. | Viscosity (Pa · s) At 37° C. |
|---|---|---|---|
| PEG200(cap$_{50}$-lac$_{50}$)$_{5.0}$-C3 | | 5.9 | 1.3 |
| 67 | 1 | 3.1 | 0.68 |
| 68 | 2 | 4.3 | 0.81 |
| PEG400(cap$_{50}$-lac$_{50}$)$_{3.0}$-C3 | | 7.8 | 1.7 |
| 69 | 1 | 1.1 | 0.31 |
| 70 | 2 | 1.1 | 0.31 |
| PEG600(cap$_{50}$-lac$_{50}$)$_{2.0}$-C3 | | 5.1 | 1.3 |
| 71 | 4 | 2.8 | 1.0 |
| 72 | 4 | 0.96 | 0.20 |
| 79 | 4 | 2.0 | 0.52 |
| 80 | 1 | 3.2 | 0.82 |
| 81 | 1 | 3.2 | 0.77 |
| PEG1000(cap$_{75}$-lac$_{25}$)$_{0.5}$-C3 | | N.A. | N.A. |
| 73 | 1 | 0.58 | 0.27 |
| 74 | 2 | 0.42 | 0.16 |

Experiment 14: In Vitro Release Formulations Loaded with 1 Lysozyme (Table 9 and Table 10)

FIG. 9 illustrates the in vitro release of lysozyme from PEG600 (cap$_{50}$-lac$_{50}$)$_{2.0}$-C3 formulations with and without a polymer surfactant. The presence of a polymer surfactant is significant. When such a polymer surfactant (formulation 71) is incorporated in the formulation, the release of lysozyme is much slower, with a very small burst for the first 24 hours. The release continued slowly to approx. 5% after 7 days. Whereas formulation 77 (without surfactant) shows a release of more than 50% after 7 days.

FIG. 10 illustrates the effect of a surfactant for the formulations based on the hydrophobic triblock copolymer PEG200(cap$_{50}$-lac$_{50}$)$_{5.0}$-C3 and PEG400(cap$_{50}$-lac$_{50}$)$_{3.0}$-C3. Formulations with surfactant (67 and 69) show a much slower release compared to the two formulations (75 and 76) without a surfactant.

FIG. 11 shows the release profile of lysozyme from several different formulations. Formulation 83 for example is a thermoreversible hydrogel, which shows a very fast release of 90% after only 2 days. A small improvement in retention was obtained when dissolving/mixing the API directly with the hydrophobic triblock copolymer using method 1 (formulation 82), whereas more than 90% was released after 7 days. The addition of a surfactant (formulations 79, 80 and 81) demonstrates even more retention, especially for the first 7 days. Surprisingly, the retention of lysozyme in formulation 80 is remarkably high. After 25 days approx. 10% was released. The difference between formulations 79, 81 and formulation 80 is the composition of the triblock copolymer surfactant. When the ratio caprolactone/lactide in the polymer surfactant was the same as the ratio in the hydrophobic triblock copolymer, the most prolonged retention and slowest release was obtained.

TABLE 11

Formulations with three different surfactants

| Formulation # | Preparation method # | hydrophobic triblock copolymer | polymer surfactant (1 wt %) |
|---|---|---|---|
| 112 | 1 | PEG600(cap$_{50}$-lac$_{50}$)$_{2.0}$-C3 | PEG1500(cap$_{50}$-lac$_{50}$)$_{2.2}$-C2 |
| 113 | 1 | PEG600(cap$_{50}$-lac$_{50}$)$_{2.0}$-C3 | PEG1500(cap$_{80}$-lac$_{80}$)$_{2.2}$-C2 |
| 114 | 1 | PEG600(cap$_{50}$-lac$_{50}$)$_{2.0}$-C3 | Pluronics 17R4 |

To further investigate this phenomenon a new set of formulations were prepared (Table 11) with different surfactants, followed by an in vitro release study. As shown in FIG. 12 the composition of the surfactant has a tremendous effect on the release of lysozyme. Pluronics17R4 as surfactant (formulation 114) does not show any form of retention, with a release of almost 100% in the first 24 hours. A polymer surfactant composed out of the same building blocks, but a different ratio in the two monomers (formulation 113), demonstrates more retention with a final release of approx. 85% after 7 days. Changing the composition of the polymer surfactant to the same ratio between the two monomers of the hydrophobic triblock copolymer surprisingly shows a tremendous retention (formulation 112). After 7 days only 20% of lysozyme was released.

Experiment 15: Preparation of Formulations Loaded with IgG

A new series of formulations were prepared with IgG as an API. Preparation method 5 was used.

TABLE 12

Formulations loaded with IgG

| # | hydrophobic triblock copolymer | Surfactant | Water (wt %) | Loading IgG (mg/ml) |
|---|---|---|---|---|
| 104 | PEG200(cap$_{75}$-lac$_{25}$)$_{4.0}$-C3 | 1% PEG1500(cap$_{80}$-lac$_{20}$)$_{2.2}$-C2 | 10 | 2.5 |
| 105 | PEG200(cap$_{75}$-lac$_{25}$)$_{4.0}$-C3 | 1% PEG1500(cap$_{50}$-lac$_{50}$)$_{2.2}$-C2 | 10 | 2.5 |
| 106 | PEG600(cap$_{50}$-lac$_{50}$)$_{2.0}$-C3 | 1% PEG1500(cap$_{80}$-lac$_{20}$)$_{2.2}$-C2 | 10 | 2.5 |
| 107 | PEG600(cap$_{50}$-lac$_{50}$)$_{2.0}$-C3 | - - - | 10 | 2.5 |
| 108 | PEG600(cap$_{50}$-lac$_{50}$)$_{2.0}$-C3 | 0.5% PEG1500(cap$_{80}$-lac$_{20}$)$_{2.2}$-C2 | 10 | 2.5 |
| 109 | PEG600(cap$_{50}$-lac$_{50}$)$_{2.0}$-C3 | 0.5% PEG1500(cap$_{80}$-lac$_{20}$)$_{2.2}$-C2 | 5 | 1.25 |
| 110 | PEG600(cap$_{50}$-lac$_{50}$)$_{2.0}$-C3 | 1% PEG1500(cap$_{80}$-lac$_{20}$)$_{2.2}$-C2 | 20 | 2.5 |
| 111 | PEG600(cap$_{50}$-lac$_{50}$)$_{2.0}$-C3 | 1% PEG1500(cap$_{50}$-lac$_{50}$)$_{2.2}$-C2 | 10 | 2.5 |

Experiment 16: Viscosity Measurements Formulations with IgG and IVR

TABLE 13

Viscosity of formulations loaded with IgG

| Formulation # | Preparation method # | Viscosity (Pa · s) At 20° C. | At 37° C. |
|---|---|---|---|
| PEG200(cap$_{75}$-lac$_{25}$)$_{4.0}$-C3 | | 0.94 | 0.33 |
| 104 | 5 | 1.1 | 0.36 |
| 105 | 5 | 1.1 | 0.35 |
| PEG600(cap$_{50}$-lac$_{50}$)$_{2.0}$-C3 | | 5.1 | 1.3 |
| 106 | 5 | 3.0 | 0.72 |
| 107 | 5 | 2.7 | 0.73 |
| 108 | 5 | 2.6 | 0.65 |
| 109 | 5 | 3.0 | 0.77 |
| 110 | 5 | 3.1 | 0.87 |
| 111 | 5 | 2.9 | 0.74 |

FIG. 13 shows the release of IgG of formulations 106 and 111 illustrates again the remarkable effect of the surfactant.

A fast release was observed for formulation 106, after 14 days more than 80% of IgG was released. Replacing the surfactant with PEG1500(cap$_{50}$-lac$_{50}$)$_{2.2}$-C2 increases the retention (formulation 111), as also seen with the lysozyme release, whereas only approx. 15% was released after 15 days.

Experiment 17: Preparation of Formulations (Monomer p-Dioxanone) Loaded with 1 wt % Lysozyme

TABLE 14

Triblock composition with caprolactone and dioxanone

| Formulation # | Preparation method # | hydrophobic triblock copolymer | Surfactant (1 wt %) |
|---|---|---|---|
| 85 | 2 | PEG600(cap$_{50}$-diox$_{50}$)$_{2.0}$-C3 | PEG1500(cap$_{50}$-lac$_{50}$)$_{2.2}$-C2 |
| 86 | 2 | PEG600(cap$_{50}$-diox$_{50}$)$_{2.0}$-C3 | PEG1500(cap$_{80}$-lac$_{20}$)$_{2.2}$-C2 |
| 87 | 2 | PEG600(cap$_{50}$-diox$_{50}$)$_{2.0}$-C3 | PEG1500(cap$_{50}$-diox$_{50}$)$_{1.8}$-C2 |
| 88 | 2 | PEG600(cap$_{50}$-diox$_{50}$)$_{2.0}$-C3 | PEG1500(cap$_{80}$-diox$_{20}$)$_{1.8}$-C2 |

TABLE 15

Viscosity triblock copolymer formulations with caprolactone and dioxanone building blocks

| Formulation # | Preparation method # | Viscosity (Pa · s) At 20° C. | At 37° C. |
|---|---|---|---|
| PEG600(cap$_{50}$-diox$_{50}$)$_{2.0}$-C3 | | 0.83 | 0.30 |
| 85 | 2 | 0.53 | 0.21 |
| 86 | 2 | 0.66 | 0.23 |
| 87 | 2 | 0.57 | 0.25 |
| 88 | 2 | 0.65 | 0.23 |

Most of this work is done using the monomers ε-caprolactone and lactide. Some experiments were also done with the monomer combination ε-caprolactone and p-dioxanone.

A Series of Formulations was Prepared with Hydrophobic Triblock Copolymer PEG600(Cap$_{50}$-Diox$_{50}$)$_{2.0}$-C3.

This triblock copolymer has a much lower viscosity compared to the hydrophobic triblock copolymers made-up with caprolactone/lactide B-blocks, due to the lower glass transition temperature of dioxanone. Still the viscosities of the formulations made were lower than the triblock copolymer alone, as expected.

As shown in FIG. 14 the composition of the surfactant had a significant effect on the release rate of lysozyme from the caprolactone/dioxanone based emulsions. A relatively fast release of lysozyme (approx. 50%) was measured after 7 days for the formulation with the caprolactone/lactide based surfactant. In contrast, only 25% of the lysozyme was released after 7 days for the formulation containing the surfactant with the caprolactone/dioxanone blocks.

Conclusion the usage of a surfactant shows a surprising effect on the release of lysozyme and IgG. Addition of a triblock copolymer surfactant with the same monomers and monomer ratio as the used hydrophobic triblock copolymer is critical for a slow and sustained release of lysozyme and IgG.

Experiment 18: Stability of the Formulations Loaded with IgG (0.5 mg/g)

TABLE 16

Formulation with 0.5 mg/g for stability purpose

| Formulation # | Preparation method # | hydrophobic triblock copolymer | Surfactant (1%) | Viscosity (Pa · s) |
|---|---|---|---|---|
| 115 | 5 | PEG$_{600}$(cap$_{50}$-lac$_{50}$)$_{2.0}$-C3 | PEG1500(cap$_{80}$-lac$_{20}$)$_{2.2}$-C2 | 4.0 at 20° C. |

To investigate the stability of the formulation, by comparing the IVR kinetics of a freshly prepared formulation with a formulation which was stored in the fridge (2-8° C.) for 2 weeks.

As shown in FIG. 15, about 90% of the IgG was released after 11 days from a freshly prepared formulation 115. In this experiment half of the formulation was stored in the fridge for 2 weeks, followed by a second IVR-study. Unfortunately the IVR results of the second IVR study did not match with the first IVR data. After 2 weeks storage the IgG release is much faster. Already after 3 days 50% of IgG was released, and 86% after 7 days, compared to 60% immediately after preparing the formulation.

Conclusion the IVR-results were not reproducible. The formulation was not stable for two weeks when stored in the fridge (2-8° C.).

Experiment 19: Preparation of Formulations with Two Surfactants, Loaded with IgG (2 mg/g)

TABLE 18

Formulations containing two polymer surfactants

| Formulation # | Preparation method # | hydrophobic triblock copolymer | Phosphate buffer (PB) | Surfactant |
|---|---|---|---|---|
| 116 | 5 | PEG600(cap$_{50}$-lac$_{50}$)$_{2.0}$-C3 | 9% | 1% ACEMIX |
| 117 | 5 | PEG600(cap$_{50}$-lac$_{50}$)$_{2.0}$-C3 | 13% | 1% ACEMIX + 0.5% PVP 10K |
| 118 | 5 | PEG600(cap$_{50}$-lac$_{50}$)$_{2.0}$-C3 | 12% | 2% ACEMIX |
| 119 | 5 | PEG200(cap$_{50}$-diox$_{50}$)$_{4.0}$-2-n-HD | 9% | 1% ACEMIX |

A series of formulations was prepared using phosphate buffer (PB) instead of phosphate buffer saline (PBS), furthermore two polymer surfactants were used (ACEMIX). The ACEMIX is a mix of the polymer surfactants PEG1500 (cap$_{80}$-lac$_{20}$)$_{2.2}$-C2 37 and PEG1500(cap$_{50}$-lac$_{50}$)$_{2.2}$-C2 36 in the ratio 3:1.

To investigate the stability of these formulations, a second in vitro release study was performed using the same formulation which was stored in the fridge (2-8° C.) for 2 weeks.

As shown in FIG. 16 and FIG. 17 there is a complete overlap between the fresh formulations and 2 weeks old formulations stored in the fridge at 2-8° C. The usage of two polymer surfactants greatly improved the stability of the formulation.

Conclusion

The formulations containing two surfactants were stable for at least 2 weeks at 2-8° C.

Experiment 20: Hydrophobic Triblock Copolymer Blends with ACEMIX Loaded with IgG

TABLE 18

Composition blend formulations

| Formulation # | Preparation method | Hydrophobic triblock copolymer | PB | ACE MIX | IgG |
|---|---|---|---|---|---|
| | | Blend ratio 1:1 | | | |
| 122 | 8 | PEG600(cap$_{50}$-lac$_{50}$)$_{2.0}$-C6 PEG600(cap$_{50}$-lac$_{50}$)$_{2.0}$-C3 Blend ratio 1:1 | 9% | 1% | 0.2% |
| 123 | 8 | PEG600(cap$_{50}$-lac$_{50}$)$_{2.0}$-C6 PEG600(cap$_{50}$-lac$_{50}$)$_{1.0}$-C6 | 9% | 1% | 0.2% |
| 124 | 8 | PEG600(cap$_{50}$-lac$_{50}$)$_{1.0}$-C6 | 9% | 1% | 0.2% |
| 125 | 8 | PEG600(cap$_{50}$-lac$_{50}$)$_{1.5}$-C6 | 9% | 1% | 0.2% |

TABLE 19

Viscosity blend formulations

| Formulation # | Preparation method | Viscosity (Pa · s) | |
|---|---|---|---|
| | | At 20° C. | At 37° C. |
| 122 | 8 | 3.1 | 0.8 |
| 123 | 8 | 1.5 | 0.3 |
| 124 | 8 | 0.7 | 0.2 |
| 125 | 8 | 1.5 | 0.4 |

Blends were prepared from hydrophobic triblock copolymers with the same monomer ratios, but different block lengths or different length on endcaps. Formulation 122 is a blend were only the type of end group is different. A variation only in block length was used in formulation 123 (table 18).

Formulations 124, 125 were used for comparative data.

Of the tested formulations, the hydrophobic triblock copolymer used in formulation 124 had the shortest polyester block, resulting in the fastest release (90% after 10 days, FIG. 18) and the lowest viscosity (Table 19). By increasing the polyester block ratio from 1.0 to 1.5 (formulation 125), the viscosity increased and the release of IgG was significant slower (80% after 10 days). Interestingly when a hydrophobic triblock copolymer with a polyester ratio of 1.0 and 2.0 were blended together to give an average polyester block ratio of 1.5, a formulation with different properties was obtained. This blend (formulation 123) had almost matching viscosity as the formulation 125, but a completely different release pattern. Furthermore, a blend of the same hydrophobic triblock copolymer composition with different end-caps (122) resulted in a change in viscosity (116) but also drastically altered the release kinetics.

Experiment 21: Ex-Vivo Injection of Triblock Copolymer Emulsions.

Polymer emulsions (250 µl) were injected in a rat cadaver at 37° C. (rats were sacrificed 1 minute before injection; the rats were taken from another study and not sacrificed for the purpose of the injection studies). Immediately after injection, the skin of the rat was removed. To our surprise, a nice "gummy" depot was formed, as shown in FIG. 19.

The depot formation was surprisingly fast, that even an air bubble was entrapped inside the depot.

An Overall Conclusion

The release profiles of (hydrophilic) API's can be surprisingly tuned using a hydrophobic triblock copolymer (A)

in combination with a polymer surfactant (B), in the presence of very low amounts of water. A preferred aspect herein is that the hydrophobic triblock copolymer (A) as the polymer surfactant (B) are prepared using the same monomers. Prolonged retention can be obtained in this way by changing the ratio between the monomers, dependent on the monomers and API. This can not achieved using commercially available surfactants.

To prolong the low temperature stability of some formulations a mixture of polymer surfactant (acemix) can be advantageously applied.

What is claimed is:

1. A composition, comprising:
   a) 55-98.9 wt. % of at least one type of triblock copolymer (A) of formula (1)

R—B-A-B—R     (1)

b) 0.1-15 wt. % of at least one surfactant (B) and
   c) 1-30 wt. % of water,
   wherein A is a hydrophilic block having a number average molecular weight (Mn) of 100-1,000 Da, B is a hydrophobic block made from monomers comprising at least a monomer B1 and a monomer B2, wherein B1 and B2 have the largest weight contents in the hydrophobic block and B1 has a lower molecular weight than B2, wherein R is an end group which is H or a C1-030 organic moiety, wherein the composition is fluid in a temperature range of 0° C. to 37° C., wherein the weight % are relative to the sum of a), b) and c), and wherein the sum of components a), b) and c) is at least 80 wt. % of the entire composition.

2. The composition according to claim 1, wherein the composition has a viscosity determined at 20° C. having a value below 30 Pa·s, as determined by shear rheology.

3. The composition according to claim 1, wherein the copolymer (A) has a Tg (midpoint) below −20° C., and/or wherein the copolymer (A) has a Tm (midpoint) below 20° C., and wherein Tg and Tm are determined with DSC, second heating curve with heating of 2° C./min.

4. The composition according to claim 1, wherein the copolymer (A) has a number average molecular weight (Mn) between 500 and 5,000 Da, as determined with size exclusion chromatography.

5. The composition according to claim 1, wherein copolymer (A) has an A block of polyethylene glycol and wherein the A block has a number average molecular weight (Mn) of at least 150 Da, and wherein the number average molecular weight of the A block is at most 1,000 Da.

6. The composition according to claim 1, wherein R is chosen from the group consisting of an acetyl group, a propionyl group, a hexanoyl group, a 2-n-hexyldecanoyl group, a nonanoyl group, a dodecanoyl group, pentadecanoyl group, a stearoyl group or a benzoyl group.

7. The composition according to claim 1, wherein the monomers B1 and B2 are selected from the group consisting of glycolide, lactide, ε-caprolactone, δ-valerolactone, 1,3-dioxan-2-one (also known as trimethylene carbonate) and 1,4-dioxan-2-one (also known as p-dioxanone), and wherein each of the B blocks have a number average molecular weight range between 200-1,500 Da.

8. The composition according to claim 1, wherein the surfactants (B) are molecules according to the formula 2 (polymer surfactant (B)):

Rs-Bs-As-Bs-Rs     formula 2 wherein As is a hydrophilic block having an number average molecular weight (Mn) of at least 1,000 Da, Bs is a hydrophobic block made from monomers comprising at least a monomer Bs1 and a monomer Bs2 wherein Bs1 and Bs2 have the largest weight contents in the hydrophobic block and Bs1 has a lower molecular weight than Bs2 and Rs is an end-group which is H or a C1-C30 organic moiety.

9. The composition according to claim 8, wherein As is a linear polyethylene glycol block, having a number average molecular weight (Mn) of between 1,000-3,000 Da, determined with size exclusion chromatography; wherein Bs are hydrophobic blocks comprising at least two cyclic monomers selected from the group consisting of lactide, ε-caprolactone, glycolide, p-dioxanone, trimethylene carbonate, δ-valerolactone, each Bs-block having a number average molecular weight (Mn) of between 400-3,000 Da, determined with size exclusion chromatography; and wherein Rs is an end-group which is H or a C1-C20 fatty acid residue.

10. The composition according to claim 8, wherein the monomer B1 and the monomer Bs1 are the same and the monomer B2 and the monomer Bs2 are the same and preferably monomers for making the polymer block B consist of monomers B1 and B2 and monomers for making the polymer block Bs consist of monomers Bs1 and Bs2.

11. The composition according to claim 8, wherein the difference between X and Xs is less than 20 wt %, wherein X is the amount of the monomer B1 with respect to the total weight of the monomer B1 and the monomer B2 and Xs is the amount of the monomer Bs1 with respect to the total weight of the monomer Bs1 and the monomer Bs2.

12. The composition according to claim 1, wherein the composition comprises between 0.01 and 15 wt. % of an active pharmaceutical ingredient, relative to the total weight of the composition.

13. A medicament, comprising: the composition according to claim 1.

14. The composition according to claim 1 for use in therapy, surgery, or in vivo diagnostics.

15. A process for preparing the composition according to claim 12, comprising the step of: mixing components a), b), c) and the therapeutically active agent.

16. The composition of claim 1, wherein the sum of components a), b) and c) is at least 90 wt. % of the entire composition, wherein the composition has a viscosity determined at 20° C. having a value below 20 Pa·s as determined by shear rheology, wherein the copolymer (A) has a Tg (midpoint) below −30° C., wherein the copolymer (A) has a Tm (midpoint) below 10° C., wherein the copolymer (A) has a number average molecular weight (Mn) between 600 and 3,000 Da, wherein the A block has a number average molecular weight (Mn) of at least 120 Da, and wherein each of the B blocks have a number average molecular weight range between 225-1,250 Da.

17. The composition of claim 16, wherein the composition has a viscosity determined at 20° C. having a value below 10 Pa·s, as determined by shear rheology, wherein the copolymer (A) has a Tg (midpoint) below −40° C., and/or wherein the copolymer (A) has a Tm (midpoint) below 0° C., wherein the copolymer (A) has a number average molecular weight (Mn) between 700 and 2,500 Da, as determined with size exclusion chromatography, wherein copolymer (A) has an A block of polyethylene glycol and wherein the A block has a number average molecular weight (Mn) of at least 150 Da, and wherein each of the B blocks have a number average molecular weight range between 250-1,000 Da.

18. The composition of claim 17, wherein the composition has a viscosity determined at 20° C. having a value below 5 Pa·s, as determined by shear rheology, and wherein each of the B blocks have a number average molecular weight range between 300-800 Da.

19. The composition of claim 18, wherein the surfactants (B) are molecules according to the formula 2 (polymer surfactant (B)):

Rs-Bs-As-Bs-Rs          formula 2 wherein As is a hydrophilic block having an number average molecular weight (Mn) of at least 1,000 Da, Bs is a hydrophobic block made from monomers comprising at least a monomer Bs1 and a monomer Bs2 wherein Bs1 and Bs2 have the largest weight contents in the hydrophobic block and Bs1 has a lower molecular weight than Bs2 and Rs is an end-group which is H or a C1-C30 organic moiety.

20. The composition of claim 19, wherein the monomer B1 and the monomer Bs1 are the same and the monomer B2 and the monomer Bs2 are the same and preferably monomers for making the polymer block B consist of monomers B1 and B2 and monomers for making the polymer block Bs consist of monomers Bs1 and Bs2, and wherein the difference between X and Xs is less than 20 wt %, wherein X is the amount of the monomer B1 with respect to the total weight of the monomer B1 and the monomer B2 and Xs is the amount of the monomer Bs1 with respect to the total weight of the monomer Bs1 and the monomer Bs2.

21. The composition of claim 8, wherein Rs is chosen from H, acetyl group, propionyl group, butyryl group, pentanoyl group, hexanoyl group, nonanoyl group, dodecanoyl group, pentadecanoyl group, 2-n-hexyldecanoyl group, stearoyl group or benzoyl group.

22. The composition of claim 19, wherein Rs is chosen from H, acetyl group, propionyl group, butyryl group, pentanoyl group, hexanoyl group, nonanoyl group, dodecanoyl group, pentadecanoyl group, 2-n-hexyldecanoyl group, stearoyl group or benzoyl group, and wherein As is a linear polyethylene glycol block, having a number average molecular weight (Mn) of between 1,000-3,000 Da, determined with size exclusion chromatography; wherein Bs are hydrophobic blocks comprising at least two cyclic monomers selected from the group consisting of lactide, ε-caprolactone, glycolide, p-dioxanone, trimethylene carbonate, δ-valerolactone, each Bs-block having a number average molecular weight (Mn) of between 400-3,000 Da, determined with size exclusion chromatography.

23. The composition of claim 19, wherein Rs is an end-group which is H or a C1-C20 fatty acid residue.

* * * * *